United States Patent
Teshima et al.

(10) Patent No.: US 10,045,753 B2
(45) Date of Patent: Aug. 14, 2018

(54) STRUCTURE, METHOD FOR MANUFACTURING THE SAME, AND TALBOT INTERFEROMETER

(71) Applicant: CANON KABUSHIKI KAISHA, Tokyo (JP)

(72) Inventors: Takayuki Teshima, Yokohama (JP); Arisa Oka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 225 days.

(21) Appl. No.: 14/804,784

(22) Filed: Jul. 21, 2015

(65) Prior Publication Data
US 2016/0027546 A1 Jan. 28, 2016

(30) Foreign Application Priority Data

Jul. 24, 2014 (JP) ................................. 2014-151202
May 29, 2015 (JP) ................................. 2015-110210

(51) Int. Cl.
| | | |
|---|---|---|
| *A61B 6/00* | (2006.01) | |
| *G21K 1/06* | (2006.01) | |
| *A61B 6/03* | (2006.01) | |
| *C25D 5/02* | (2006.01) | |
| *G21K 1/10* | (2006.01) | |

(52) U.S. Cl.
CPC .............. *A61B 6/484* (2013.01); *A61B 6/032* (2013.01); *A61B 6/4035* (2013.01); *C25D 5/02* (2013.01); *G21K 1/062* (2013.01); *G21K 1/067* (2013.01); *G21K 1/10* (2013.01); *G21K 2201/061* (2013.01); *G21K 2201/067* (2013.01); *G21K 2207/005* (2013.01)

(58) Field of Classification Search
CPC ....... A61B 6/032; A61B 6/4035; A61B 6/484; G21K 1/067
USPC ..................... 378/36, 62, 147, 149
See application file for complete search history.

(56) References Cited

U.S. PATENT DOCUMENTS

| | | | | |
|---|---|---|---|---|
| 4,393,127 A * | 7/1983 | Greschner | ................. | G03F 1/20 250/503.1 |
| 4,902,379 A | 2/1990 | Rhodes | | |
| 6,018,566 A * | 1/2000 | Eberhard | ............... | G21K 1/025 378/145 |
| 6,531,392 B2 * | 3/2003 | Song | ................. | G02F 1/134363 257/E21.414 |
| 7,087,474 B2 * | 8/2006 | Mitsuda | ............ | H01L 21/02063 257/E21.228 |

(Continued)

FOREIGN PATENT DOCUMENTS

| | | |
|---|---|---|
| CN | 1257304 A | 6/2000 |
| CN | 101939667 A | 1/2011 |

(Continued)

*Primary Examiner* — Allen C. Ho
(74) *Attorney, Agent, or Firm* — Canon U.S.A., Inc. IP Division

(57) ABSTRACT

A structure includes a silicon substrate having a plurality of recessed portions, each recessed portion having a bottom and a side wall, silicide layers, each silicide layer in contact with the bottoms of the plurality of recessed portions, and a metal structure including metal portions, each metal portion disposed in the plurality of recessed portions and in contact with the silicide layers. The silicide layers are electrically connected to each other through the silicon substrate.

2 Claims, 14 Drawing Sheets

(56) References Cited

U.S. PATENT DOCUMENTS

| | | | | |
|---|---|---|---|---|
| 7,749,840 B2* | 7/2010 | Yun | H01L 27/10885 | 438/257 |
| 7,786,538 B2* | 8/2010 | Tsuchiaki | H01L 21/32 | 257/382 |
| 7,807,975 B2* | 10/2010 | Schmitt | G01T 1/20 | 250/368 |
| 7,949,095 B2* | 5/2011 | Ning | A61B 6/032 | 378/4 |
| 8,319,288 B2* | 11/2012 | Masuoka | H01L 21/823821 | 257/369 |
| 8,373,235 B2* | 2/2013 | Masuoka | H01L 27/0886 | 257/368 |
| 8,532,252 B2* | 9/2013 | Nakamura | G21K 1/06 | 378/145 |
| 8,767,914 B2* | 7/2014 | Teshima | C25D 5/022 | 378/145 |
| 8,831,174 B2* | 9/2014 | Kohara | A61B 6/06 | 378/62 |
| 8,848,863 B2* | 9/2014 | Schusser | G21K 1/06 | 378/16 |
| 8,855,265 B2* | 10/2014 | Engel | A61B 6/00 | 378/36 |
| 8,895,934 B2* | 11/2014 | Wang | B81C 1/00619 | 250/363.06 |
| 8,908,274 B2* | 12/2014 | Teshima | G21K 1/06 | 359/563 |
| 8,913,714 B2* | 12/2014 | Michel | A61B 6/484 | 250/370.09 |
| 8,989,353 B2* | 3/2015 | Kaneko | G21K 1/025 | 378/145 |
| 8,999,435 B2* | 4/2015 | Setomoto | B29D 11/00769 | 427/160 |
| 9,060,736 B2* | 6/2015 | Nakamura | A61B 6/484 | |
| 9,066,704 B2* | 6/2015 | Den | G01N 23/046 | |
| 9,228,961 B2* | 1/2016 | Teshima | G01N 23/20008 | |
| 9,240,330 B2* | 1/2016 | Takeda | H01L 21/486 | |
| 9,263,162 B2* | 2/2016 | Teshima | C25D 1/08 | |
| 9,348,067 B2* | 5/2016 | Vogtmeier | G02B 5/1857 | |
| 9,364,191 B2* | 6/2016 | Ning | A61B 6/032 | |
| 9,385,080 B2* | 7/2016 | Lin | H01L 23/528 | |
| 9,506,878 B2* | 11/2016 | Teshima | A61B 6/4035 | |
| 9,748,012 B2* | 8/2017 | Yokoyama | G21K 1/06 | |
| 9,826,949 B2* | 11/2017 | Ning | A61B 6/484 | |
| 9,891,327 B2* | 2/2018 | Teshima | G01T 1/16 | |
| 2008/0268635 A1 | 10/2008 | Yu et al. | | |
| 2009/0196399 A1 | 8/2009 | Schmitt | | |
| 2011/0168908 A1 | 7/2011 | Shinan et al. | | |
| 2011/0182403 A1 | 7/2011 | Nakamura | | |
| 2012/0002785 A1* | 1/2012 | Kaneko | G21K 1/067 | 378/62 |
| 2012/0012754 A1* | 1/2012 | Kaneko | G02B 5/1857 | 250/393 |
| 2012/0051508 A1* | 3/2012 | Kaneko | A61B 6/4035 | 378/62 |
| 2012/0051509 A1* | 3/2012 | Kaneko | A61B 6/4035 | 378/62 |
| 2012/0099706 A1* | 4/2012 | Kaneko | C25D 3/48 | 378/87 |
| 2012/0148029 A1* | 6/2012 | Kaneko | G21K 1/06 | 378/154 |
| 2012/0163535 A1* | 6/2012 | Kaneko | A61B 6/4291 | 378/62 |
| 2012/0183124 A1* | 7/2012 | Kaneko | A61B 6/4291 | 378/62 |
| 2012/0201349 A1* | 8/2012 | Kaneko | A61B 6/4035 | 378/62 |
| 2012/0285518 A1 | 11/2012 | De Souza et al. | | |
| 2013/0051530 A1 | 2/2013 | Nepomnishy et al. | | |
| 2013/0052826 A1 | 2/2013 | Nepomnishy et al. | | |
| 2013/0252416 A1 | 9/2013 | Yasuhiro et al. | | |
| 2014/0241493 A1* | 8/2014 | Yokoyama | G01N 23/20008 | 378/36 |
| 2015/0131783 A1* | 5/2015 | Sato | G01T 1/2928 | 378/82 |
| 2015/0137323 A1* | 5/2015 | Zhou | H01L 21/76898 | 257/621 |
| 2015/0179292 A1* | 6/2015 | Sato | G21K 1/067 | 378/154 |

FOREIGN PATENT DOCUMENTS

| | | | |
|---|---|---|---|
| CN | 102741709 A | 10/2012 | |
| EP | 0911836 A1 | 4/1999 | |
| JP | 2009-37023 A * | 2/2009 | G02B 5/18 |
| JP | 2010-185728 A | 8/2010 | |
| JP | 2011-157622 A | 8/2011 | |
| JP | 2012-149953 A | 8/2012 | |
| JP | 2013-049923 A | 3/2013 | |
| JP | 2013-122487 A | 6/2013 | |
| JP | 2013-201353 A | 10/2013 | |
| JP | 2014-090200 A | 5/2014 | |
| WO | 2011/122506 A1 | 10/2011 | |
| WO | 2013/129309 A1 | 9/2013 | |
| WO | 2014/204620 A1 | 12/2014 | |

* cited by examiner

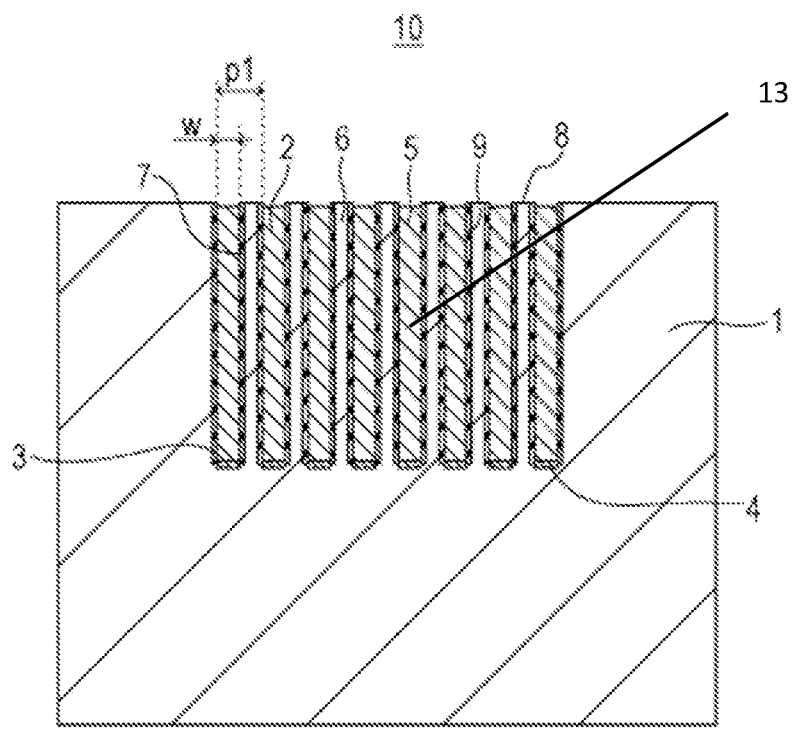
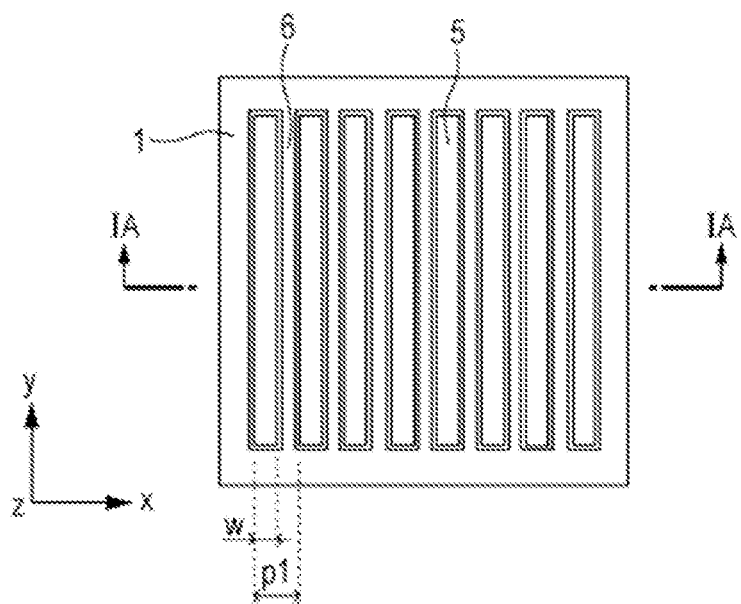

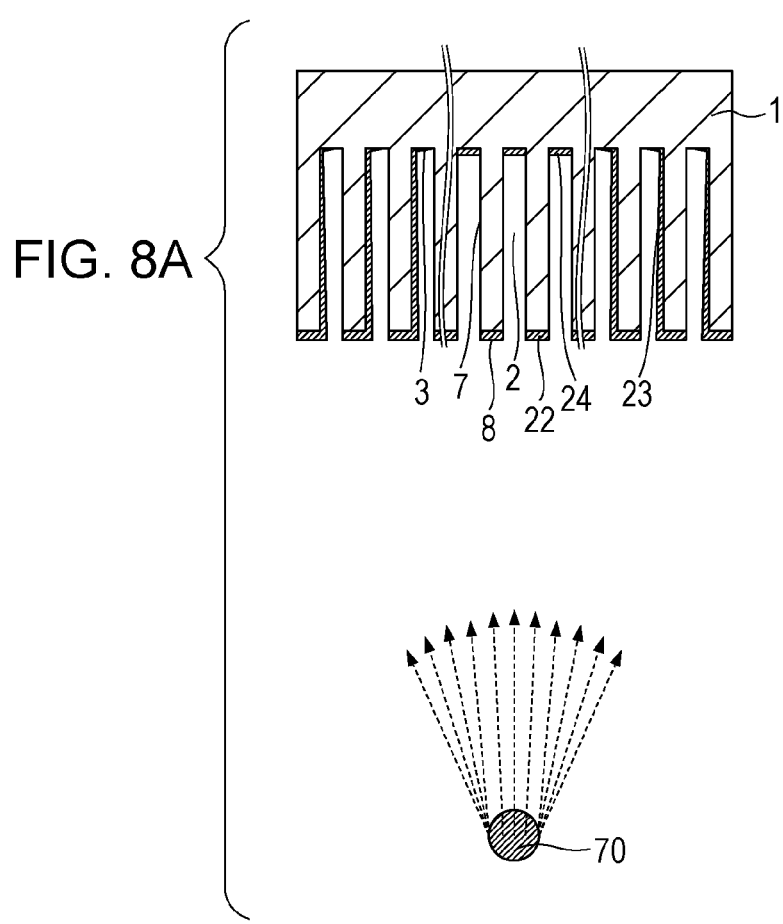

US 10,045,753 B2

STRUCTURE, METHOD FOR MANUFACTURING THE SAME, AND TALBOT INTERFEROMETER

BACKGROUND OF THE INVENTION

Field of the Invention

The present disclosure relates to a structure, a method for manufacturing the structure, and a Talbot interferometer.

Description of the Related Art

Diffraction gratings having periodic structures are used as optical elements in various types of apparatus. In particular, structural bodies made of a metal having a high X-ray absorptance are used for nondestructive inspection, medical practice and the like.

One of the applications of structural bodies made of a metal having a high X-ray absorptance is the shield grating of interferometers (X-ray Talbot interferometers) for X-ray Talbot interferometry. The X-ray Talbot interferometry is a method for collecting the information of a subject using the phase shift of X-ray waves by the subject.

The X-ray Talbot interferometry will be simply described below. A typical X-ray Talbot interferometer diffracts coherent X-ray radiation through an X-ray diffraction grating to form an interference pattern. The X-ray shield grating, which is disposed at the position where the interference pattern is formed, blocks part of X-ray radiation that is to form the interference pattern, thus forming an intensity distribution different from that of the interference pattern. The information of this intensity distribution is obtained by detecting X-ray radiation from the X-ray shield grating with an X-ray detector. The intensity distribution is changed by disposing a subject in the light path between an X-ray source and the X-ray shield grating. The information of the subject is obtained from the change of the intensity distribution.

If an X-ray source that emits low-coherent X-ray radiation is used as a light source of a Talbot interferometer, an X-ray shield grating is disposed between the X-ray source and a diffraction grating so as to form imaginarily an array of micro-focus X-ray sources, and thus coherence is given to the X-ray radiation. This technique is particularly called X-ray Talbot-Lau interferometry. In the following description, the X-ray shield grating disposed at the position where an interference pattern is formed is referred to as an analysis grating; and the X-ray shield grating disposed between an X-ray source and a diffraction grating is referred to as a source grating. The X-ray shield grating simply mentioned refers to either a source grating or an analysis grating, or both.

A typical X-ray shield grating used for Talbot interferometry has a structure in which X-ray transmission portions (may be simply referred to as transmission portions) and X-ray shield portions (may be simply referred to as shield portions) are periodically arranged. The X-ray shield portions are often made of a metal having high X-ray absorptance. Even when the shield portions are made of a metal having a high X-ray absorptance, however, the shield portions are required to have a high aspect ratio from the viewpoint of the relationship between the thickness required to block X-ray radiation and the period of the interference pattern (for the analysis grating) or the imaginary array of X-ray sources (for the source grating). In the present disclosure or the description herein, the aspect ratio of the shield portions is defined as the ratio (h/w) of the height h of the shield portion to the width w thereof.

For manufacturing such a shield grating, a process is known in which a mold is filled with a metal by plating.

Japanese Patent Laid-Open No. 2010-185728 discloses a method for manufacturing a shield grating, in which a metal is deposited by plating in recessed portions formed in a silicon substrate by reactive etching.

In this method, after protective film is formed on the bottoms and side walls of the recessed portions, the silicon substrate is exposed at the bottoms, and the exposed surface of the silicon substrate is used as a seed layer for growing a metal therefrom.

The present inventors however have found that the adhesion between the metal and the silicon substrate can be reduced depending on the metal and the magnitude of the film stress produced in the metal, and that the connection between the bottom of the recessed portion and the metal is broken in some cases by receiving a physical force.

SUMMARY OF THE INVENTION

According to an aspect of the disclosure, there is provided a structure including a silicon substrate having a plurality of recessed portions, each having a bottom and a side wall, silicide layers, one each in contact with the bottoms of the recessed portions, and a metal structure including metal portions, one each disposed in the recessed portions and in contact with the silicide layers. The silicide layers in the different recessed portions are electrically connected to each other through the silicon substrate.

Further features of the present invention will become apparent from the following description of exemplary embodiments with reference to the attached drawings.

BRIEF DESCRIPTION OF THE DRAWINGS

FIG. 1A is a schematic sectional view of a structure according to a first embodiment of the present disclosure.

FIG. 1B is a schematic top view of the structure according to the first embodiment.

FIGS. 8A to 8C are schematic representations illustrating a method for forming metal layers of the fourth embodiment.

DESCRIPTION OF THE EMBODIMENTS

Figure 2A:
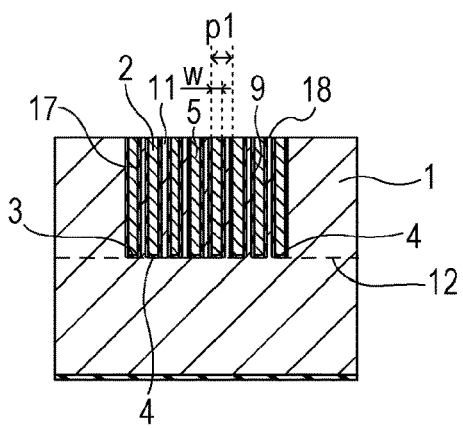
FIG. 2A is a schematic sectional view of a structure according to a second embodiment of the present disclosure.

Exemplary embodiments will now be described with reference to the drawings. In the drawings, the same parts are designated by the same reference numerals and thus description thereof is omitted.

The embodiments described below will provide structural bodies, each having higher adhesion between a silicon substrate and a metal than the case where a metal is directly deposited on a silicon substrate.

A first embodiment will describe a structure 10 including a one-dimensionally periodic structure and capable of being used as a one-dimensional X-ray shield grating. A second embodiment will describe a structure 10 including a two-dimensional periodic structure and capable of being used as a two-dimensional X-ray shield grating. A third embodiment will describe a method for manufacturing the structural bodes of the first embodiment and the second embodiment, and a fourth embodiment will describe another method for manufacturing the structural bodies of the first embodiment and the second embodiment. A fifth embodiment will describe a Talbot interferometer including the structure 10 of the first embodiment.

The first embodiment and the second embodiment are the same in that the structure 10 includes a silicon substrate 1 and a metal structure 5 in which portions of the silicon substrate 1 and metal portions 13 of the metal structure 5 are connected to each other with a silicide layer 4 there between. Since silicide has high adhesion to both silicon and metal, the silicon substrate 1 and the metal structure 5 are unlikely to separate from each other even if a physical force is placed on the structure 10.

Each embodiment will be further described in detail.

First Embodiment

The first embodiment will describe a structure including a one-dimensionally periodic structure and capable of being used as a one-dimensional X-ray shield grating.

FIG. 1A shows a schematic sectional view of the structure 10 of the present embodiment, and FIG. 1B shows a schematic top view of the structure 10. The section shown in FIG. 1A is taken along line IA-IA in FIG. 1B. As shown in FIGS. 1A and 1B, the structure 10 of the present embodiment includes a silicon substrate 1 having a plurality of recessed portions 2 therein, as plurality of silicide layers 4, one each in contact with the bottoms 3 of the plurality of recessed portions 2, and a metal structure 5 defined by metal portions 13 disposed in the plurality of recessed portions 2. The plurality of silicide layers 4 are each in contact with the metal structure 5. The plurality of silicide layers 4 in the different recessed portions 2 are separate from each other, and the metal portions 13 of the metal structure 5 disposed in the plurality of recessed portions 2 are also separate from each other. In other words, the silicon substrate 1 has a plurality of recessed portions 2 therein, each in which are disposed the plurality of silicide layers 4 in contact with the bottom 3 of the plurality of recessed portion 2 and the metal portion 13 of the metal structure 5 in contact with the corresponding plurality of silicide layers 4. The metal portions 13 of the metal structure 5 are arranged at a pitch p1 in the x-axis direction. The width w and pitch p1 of the metal portions 13 of the metal structure 5 are not particularly limited. The width w of the metal portion 13 is a length thereof in the direction in which the metal portions 13 are arranged, that is, in the x-axis direction.

If the structure 10 is used as an X-ray shield grating, the metal portions of the metal structure 5 function as shield portions that block X-ray radiation, and the portions 6 of the silicon substrate 1 between the metal portions function as transmission portions through which X-ray radiation is transmitted. If the structure 10 is used as an X-ray shield grating, the structure 10 is often used such that X-ray radiation travels along the z axis perpendicular to the x axis and the y axis (if x-ray radiation travels different directions, in the direction along the center line of the X-ray flux). In this instance, the width w of the metal portions of the metal structure 5 defines the width of the X-ray shield portion, and the pitch p1 of the metal structure 5 defines the pitch of the X-ray shield grating. The width w of the metal portions and the pitch p1 of the metal structure are set according to the shape of the desired X-ray shield grating.

The plurality of recessed portions 2 may be formed in the silicon substrate 1 by any method without particular limitation, and for example, by anisotropic etching. The plurality of recessed portions 2 may be formed using a photosensitive resist for a different structure from the structure 10 shown in FIGS. 1A and 1B. In this instance, the plurality of recessed portions 2 are formed by forming a resist layer having a plurality of through holes therein on the silicon substrate 1. The resist layer is formed by applying the photosensitive resist onto the silicon substrate 1, patterning the resist, and removing uncured portions of the resist, as disclosed in Japanese Patent Laid-Open No. 2009-37023. Each of the thus formed plurality of recessed portions 2 has a side wall defined by the side wall of the through hole in the resist layer, and a bottom 3 defined by the surface of the silicon substrate 1 exposed by removing the uncured resist. The silicon substrate 1 in this structure 10 serves in part as portions defining the plurality of recessed portions 2, and therefore the silicon substrate 1 provided with a layer having through holes therein is also referred to as the silicon substrate 1 having a plurality of recessed portions 2.

The adhesion between silicide and metal is generally higher than the adhesion between silicon and metal, and accordingly the adhesion between the plurality of silicide layers 4 and the metal structure 5 is higher. Therefore the silicon substrate 1 and the metal structure 5 are unlikely to separate from each other even if a physical force is placed on the structure 10. It is desirable that the surface of the metal structure 5 in contact with the plurality of silicide layers 4 contains the same metal as the metal contained in the plurality of silicide layers 4 (that is, the metal in the silicide of the plurality of silicide layers 4). In other words, when the silicide of the plurality of silicide layers 4 is a compound containing silicon and at least one of the same metals as the metal constituents of the surface of the metal structure 5 in contact with the plurality of silicide layers 4, the adhesion between the plurality of silicide layers 4 and the metal structure 5 is advantageously increased. The same metal mentioned herein refers to the same element. For example, when the metal structure 5 is made of gold, it is desirable to form the plurality of silicide layers 4 of gold silicide. When the surface of the metal structure 5 in contact with the plurality of silicide layers 4 is made of an alloy, it is desirable to form the plurality of silicide layers 4 of a compound containing silicon and at least one of the metal elements in this alloy. In this instance, more desirably, the plurality of silicide layers 4 contain the metal element having the highest content of the metal elements in the alloy. For example, when the surface of the metal structure 5 in contact with the plurality of silicide layers 4 is formed of an alloy of gold and copper, the plurality of silicide layers 4 may be made of a compound containing gold, copper and silicon, a compound of gold and silicon, or a compound containing copper and silicon. In this instance, however, if the alloy of the surface of the metal structure 5 in contact with the plurality of silicide layers 4 contains more gold than copper, a compound of gold and silicon is more advantageous for the plurality of silicide layers 4 than a compound of copper and silicon. In the case where the metal portions 13 of the metal structure 5 have a multilayer structure, it is desirable that the surface thereof in contact with the plurality of silicide layers 4 contain the same metal as the metal contained in the plurality of silicide layers 4. For example, if the surface of the metal structure 5 in contact with the plurality of silicide layers 4 is made of nickel and the layer overlying the nickel layer is made of gold, the plurality of silicide layers 4 is desirably made of a compound containing nickel and silicon.

In the description of this disclosure, silicide refers to amorphous silicon or crystalline silicon in which some of the silicon atoms are substituted with a metal element. If some of the silicon atoms are substituted with a metal element, some of the silicon-silicon bonds are converted into silicon-metal bonds. The constituents of the silicide are not particularly limited, and examples of the silicide include gold silicide, nickel silicide, copper silicide, titanium silicide, tungsten silicide, cobalt silicide, iron silicide, and molybdenum silicide.

The material of the metal structure 5 is not particularly limited. For the structure 10 intended for use of an X-ray shield grating, however, gold or an alloy containing gold is advantageous as the material of the metal structure 5 from the viewpoint of the magnitude of the X-ray absorptance and the ease of arrangement in the plurality of recessed portions 2. For forming a gold or gold alloy metal structure 5, a silicon substrate 1 having plurality of recessed portions 2 each in which a silicide layer is formed at the bottom of a recessed portion is subjected to electroplating as a mold. Thus gold or a gold alloy is deposited in each of the plurality of recessed portions 2. In this operation, the silicide layer is used as a seed.

In this operation, the plurality of silicide layers 4 are separate from each other, but are electrically connected through the silicon substrate 1 that is a semiconductor material. Hence, when the silicon substrate 1 having plurality of recessed portions 2 each in which a silicide layer is disposed at the bottom thereof is subjected to electroplating as a mold, each of the plurality of silicide layers 4 can be electrified through the silicon substrate 1. For electrifying the plurality of silicide layers 4, electricity may be directly supplied to the plurality of silicide layers 4 from an external power supply. Since the plurality of silicide layers 4 are separate from each other, but are electrically connected through the silicon substrate 1, all the plurality of silicide layers 4 electrically connected through the silicon substrate 1 can be electrified, as long as at least one silicide layer 4 is connected to an external power supply. The plurality of silicide layers 4 thus can be electrified from an end of the silicon substrate 1 or the surface of the silicon substrate 1 opposite the plurality of recessed portions 2, and thus the metal structure 5 can be formed in a large area of the silicon substrate 1. The phrase "electrically connected" mentioned herein means that when electricity is applied to one recessed portion, the electricity flows from the portion to the other.

If the silicon substrate 1 is exposed at the side walls 7 of the plurality of recessed portions 2 and the top surfaces 8 around the plurality of recessed portions 2, the plating metal can be deposited on the side walls 7 and the top surfaces 8. This can cause void to be formed in the metal portions 13 of the metal structure 5. In the case of using the structure 10 as an X-ray shield grating, voids in the metal structure 5 may result in uneven shield depending on the degree of the voids, the depth of the plurality of recessed portions 2 or the energy of x-ray radiation. Accordingly, for electrifying the plurality of silicide layers 4 through the silicon substrate 1 for electroplating, it is desirable to cover the side walls 7 and the top surfaces 8 with an insulating layer 9. In this instance, the side walls 7 of the plurality of recessed portions 2 are separated from the corresponding metal portions 13 of the metal structure 5 in the plurality of recessed portions 2 by the insulating layer 9 in the resulting structure 10. The insulating layer 9 is in contact with the metal structure 5 at the surface thereof opposite the surface in contact with the side wall 7. Hence, the metal portions 13 of the metal structure 5 are connected one each to the bottoms 3 of the plurality of recessed portions 2 with the plurality of silicide layer 4 there between, and to the side walls 7 of the plurality of recessed portions 2 with the insulating layer 9 there between. The insulating layer 9 may be made of any insulating material, and may be a thermally oxidized silicon film or a nitride film. The portions of the insulating layer 9 formed on the top surfaces 8 may be removed after electroplating. The top surfaces 8 around the plurality of recessed portions 2 refer to the surfaces of portions 6. For example, if the surface of the silicon substrate 1 is exposed at the top surfaces 8, the top surfaces 8 are portions of the silicon substrate 1; if the surface of the silicon substrate 1 is covered with an insulating layer 9, the top surfaces 8 are portions of the insulating layer 9. If the side walls 7 of the plurality of recessed portions 2 are defined by through holes in a resist layer and the surface of the resist layer opposite the silicon substrate 1 is exposed at the top surfaces 8, the tops surfaces 8 are portions of the resist layer.

If the structure 10 is used as an X-ray shield grating, the shield portions desirably block 80% or more of the x-ray radiation perpendicularly incident on the shield portions. Accordingly, the thickness of, for example, a gold metal structure may be 10 μm or more for x-ray radiation of 5 keV, although the thickness depends on the material of the metal structure and the energy of X-ray radiation incident on the metal structure. Advantageously, the thickness of the metal structure is smaller than or equal to the height of the recessed portions. Accordingly, the height of the recessed portions is 10 μm or more. If the structure is used as the X-ray shield grating of a Talbot interferometer, the metal portions 13 of the metal structure 5 are often arranged at a pitch p1 in the range of 2 μm to 24 μm, having a width w in the range of 0.5 μm to 12 μm. The aspect ratio of each recessed portion is often in the range of 10 to 150. If the metal structure is made of a metal other than gold, the metal structure is formed to a larger thickness, and the aspect ratio of the recessed portions is increased accordingly. If the structure 10 is used as an X-ray shield grating, the recessed portions are desirably as vertical as possible in the depth direction thereof. More specifically, the side walls 7 of the recessed portions may form an angle of 89.5 degrees to 90.5 degrees, desirably 89.8 degrees to 90.2 degrees, more desirably 89.9 degrees to 90.1 degrees, with the top surfaces 8 around the recessed portions. If the recessed portions are less vertical in the depth direction thereof, portions incapable of sufficiently blocking x-ray radiation may be formed around the side walls 7 of the recessed portions. The aspect ratio of the metal portions 13 mentioned herein is a value relative to the smallest width w of the metal portion 13.

Second Embodiment

A second embodiment will describe a structure including a two-dimensional periodic structure and capable of being used as a two-dimensional X-ray shield grating.

Figure 2B:
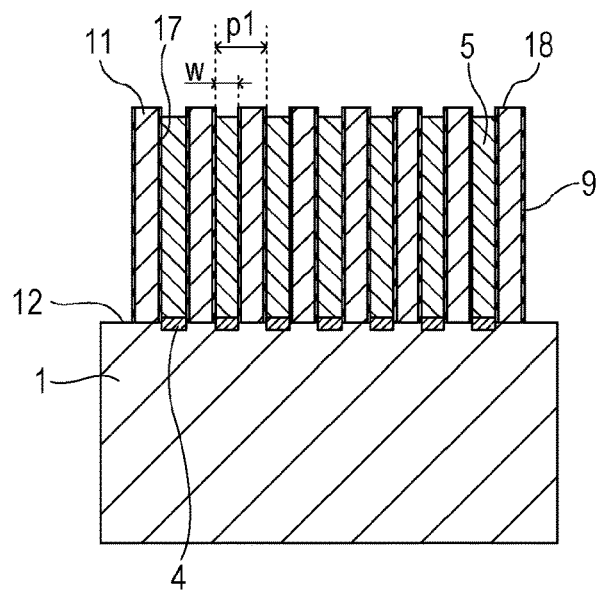
FIG. 2B is a schematic sectional view of another structure according to the second embodiment.
Figure 2C:
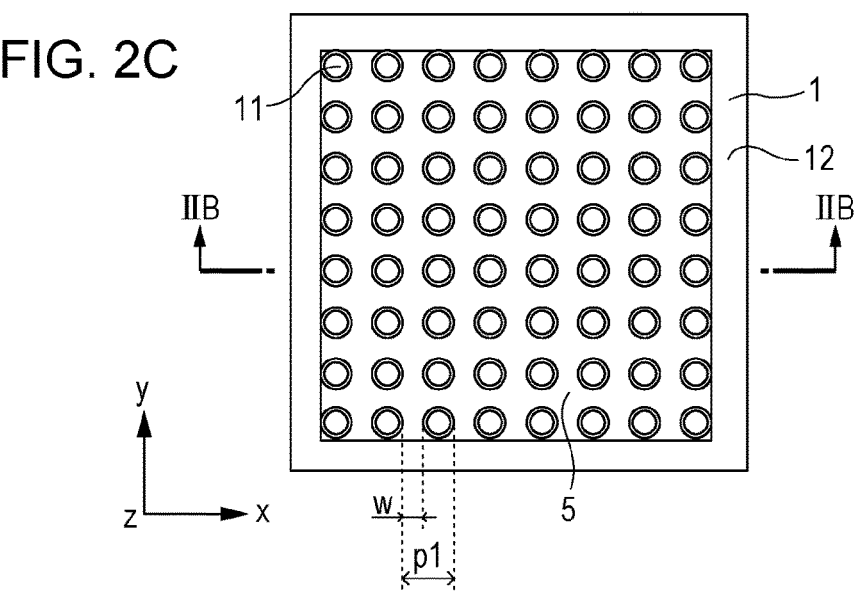
FIG. 2C is a schematic top view of the structure according to the second embodiment.

FIGS. 2A and 2B show sectional views of structural bodies according to the second embodiment, and FIG. 2C shows a top view of the structure shown in FIG. 2B. The section shown in FIG. 2B is taken along line IIB-IIB in FIG. 2C.

FIG. 2A is a sectional view of a structure 10 including a plurality of protrusion portions 11 formed by etching a silicon substrate 1. Hence, the protrusion portions 11 are each made of silicon, and are arranged on a first surface 12. The first surface 12 is an imaginary surface joining the bottoms 3 of recessed portions 2 formed by etching.

The structure 10 shown in FIG. 2A includes a silicon substrate 1 having a first surface 12 on which the plurality of protrusion portions 11 are arranged, silicide layers 4, and a metal structure 5. The silicide layers 4 are disposed one each in the regions of the first surface 12 between the protrusion portions (hereinafter often referred to as regions between the protrusion portions) so as to be in contact with the regions. The regions between the protrusion portions are defined by a surface of the silicon substrate. The metal structure 5 is disposed so as to fill the spaces between the protrusion portions, thus surrounding the protrusion portions. In other words, the metal structure 5 has a plurality of holes corresponding to the protrusion portions. Hence, the structure 10 can be such that the metal structure is disposed so as to fill the spaces between the silicon protrusion portions arranged in the silicon substrate.

On the other hand, FIG. 2B is a sectional view of a structure 10 including a plurality of protrusion portions formed on a first surface 12 of a silicon substrate 1. As with the structure shown in FIG. 2A, the structure 10 shown in FIG. 2B includes a silicon substrate 1 having the first surface 12 on which the plurality of protrusion portions 11 are arranged, silicide layers 4 one each disposed in the regions between the protrusion portions 11, and a metal structure 5. The structure of FIG. 2B is however different from that of FIG. 2A in that the silicon substrate 1 and the protrusion portions 11 are not formed from the same silicon substrate. The protrusion portions 11 may be made of any material without particular limitation. In the structure 10 intended for X-ray shield grating, however, the protrusion portions are made of a material having a high X-ray transmittance so as to be able to function as transmission portions. Desirably, the material of the protrusion portions 11 is selected so that each protrusion portion 11 can transmit 80% or more of the X-ray radiation perpendicularly incident on the protrusion portion. A photosensitive resist may be used as the material of the protrusion portions 11. The photosensitive resist can form microscopic protrusion portions 11 arranged at a very small pitch in a process performed by applying the photosensitive resist, patterning the resist, and removing uncured portions of the resist, as in the first embodiment. In this instance, the photosensitive resist comes in contact with the surface of the silicon substrate. For forming the protrusion portions on the silicon substrate in this manner, the silicon substrate may have a structure including a substrate made of a material other than silicon and a silicon layer on at least one surface of the substrate. The sectional view of FIG. 2B shows portions of the metal structure 5 disposed in the spaces between the protrusion portions, and the portions are seemed to be separate from each other. The metal structure 5 is however integrated into one body in depth direction of the figure (FIG. 2C). This applies to the structure 10 shown in FIG. 2A. Although the metal structure 5 shown in FIG. 2C is rectangular in outline, many portions of the edges of the metal structure not defined by the protrusion portions are not straight. The metal portions 13 of the metal structure 5 disposed between the recessed portions 2 may be separate from each other. If the regions of the silicon substrate between the protrusion portions are separate from each other, the metal structure is defined by the separate metal portions. Silicide layers one each in contact with the separate metal portions 13 of the metal structure 5 are also separate from each other, but are electrically connected to each other through the silicon substrate.

The common points will now be described between the structure 10 as shown in FIG. 2A including the protrusion portions 11 formed by etching the silicon substrate 1 and the structure 10 as shown in FIG. 2B including the protrusion portions 11 formed on the silicon substrate 1.

The width and pitch of the protrusion portions 11 and the pattern of the protrusion portion arrangement are not particularly limited. For example, the protrusion portions 11 may be arranged so as to form a mesh-like metal structure as shown in FIG. 2C, or a checkerboard-like metal structure. For forming a mesh-like metal structure, for example, the protrusion portions may be arranged in each intersection of a grid like a graph paper. For forming a checkerboard-like metal structure, for example, the protrusion portions may be arranged in each intersection of a grid like a graph paper and the barycenters of each square of the grid. The pitch of the protrusion portions 11 need not be the same between the x-axis direction and the y-axis direction, and the shape defined by lines of the grid like a graph paper may be rectangular.

If the structure 10 is used as an X-ray shield grating, the metal structure 5 functions as shield portions that block X-ray radiation, and the protrusion portions 11 function as transmission portions through which X-ray radiation is transmitted. In the case of being used as an X-ray shield grating, the structure 10 is often used such that X-ray radiation travels along the z axis, as in the first embodiment. Accordingly, the width w and pitch p1 of the metal portions 13 of the metal structure 5 are set according to the desired shape of the X-ray shield grating. The width w of the metal portions 13 of the metal structure 5 is the smallest length of each metal portion 13 in the direction in which the protrusion portions are arranged (x-axis and y-axis directions), that is, the smallest length of the spaces between the protrusion portions in the directions of the arrangement of the protrusion portions. Also, the pitch p1 of the metal portions 13 of the metal structure 5 is equal to the pitch of the arrangement of the protrusion portions.

The structure of the present embodiment is the same as that of the first embodiment except that the periodic structure is two-dimensional. If the surface of the metal structure in contact with the silicide layers contains the same metal as the metal contained in the silicide layer, the adhesion between the silicide layer and the metal structure is advantageously increased. In the case of using the structure 10 as an X-ray shield grating, this surface of the metal structure is desirably made of gold or an alloy containing gold. For forming the metal structure of gold or an alloy containing gold, the spaces between the protrusion portions are filled with gold or the alloy containing gold by electroplating. For this electroplating, it is desirable to cover the side walls 17 and top surfaces 18 of the protrusion portions with an insulating layer 9. In this instance, the protrusion portions 11 and the metal portions 13 of the metal structure 5 in the spaces between the protrusion portions 11 are separated by the respective insulating layers 9 in the resulting structure 10. Each of the insulating layer 9 formed on the side walls 17 is in contact with the metal structure 5 at the surface thereof opposite the surface in contact with the side wall 17. Hence, each metal portion 13 of the metal structure 5 is connected to the first surface 12 with the silicide layer 4 therebetween, and to the side wall 17 of the protrusion portion 11 with the insulating layer 9 therebetween.

In the case of using the structure 10 as an X-ray shield grating, the shield portions block, desirably, 80% or more of the x-ray radiation perpendicularly incident on the shield portions, as in the first embodiment. Advantageously, the thickness of the metal structure is smaller than or equal to the height of the protrusion portions. If the structure is used as the X-ray shield grating of a Talbot interferometer, the protrusion portions are often arranged at a pitch p1 in the range of 2 μm to 24 μm, and the width w of the transmission portions is in the range of 1 μm to 12 μm. The aspect ratio of each protrusion portion is often in the range of 10 to 150. If the metal structure is made of a metal other than gold, the metal structure is formed to a larger thickness, and the aspect ratio of the protrusion portions is increased accordingly. The side wall 17 of the protrusion portion may form an angle of 89.5 degrees to 90.5 degrees, desirably 89.8 degrees to 90.2 degrees, more desirably 89.9 degrees to 90.1 degrees, with the top surface 18 of the substrate.

Third Embodiment

Methods for manufacturing the structural bodies according to the first and second embodiments will now be described in detail.

A method for manufacturing the structure of the first embodiment will first be described with reference to FIGS. 3A to 3G. The method for manufacturing the structure of the first embodiment includes the following steps (1) and (2) of:
(1) forming silicide layers 4 by heating a silicon substrate 1 having a plurality of recessed portions 2 each provided with a metal layer 22 on the bottom 3 thereof, thus forming the silicide layers 4 at the interfaces between the bottoms 3 of the recessed portions 2 and the metal layers 22; and
(2) forming a metal structure 5 by electroplating for filling each recessed portion, at least in part, with a metal.

These steps will now be described.
(1) Step of Forming Silicide Layers

The step of forming silicide layers includes preparing a silicon substrate having a plurality of recessed portions each provided with a metal layer on the bottom thereof, and heating the silicon substrate to form silicide.

The silicon substrate having the recessed portions each provided with a metal layer on the bottom thereof may be prepared in any process without particular limitation. Such a silicon substrate may be fabricated or purchased. In the present embodiment, a p-type or n-type semiconductor silicon substrate is used as the silicon substrate 1. The use of a p-type or an n-type silicon semiconductor silicon substrate enables electroplating through the silicon substrate 1, and is thus advantageous.

The silicon substrate is such that regions (p-n junction diodes) where p-type semiconductor changes into n-type semiconductor and vice versa will not be formed in the silicon portions under the silicide layers and between the silicide layers. For example, a structure having n-type silicon portions under the adjacent silicide portions and a p-type silicon portion between the silicide portions does not allow forward current to flow. This suggests that the adjacent silicide layers cannot be electrically connected to each other through the silicon substrate. The phrase "silicide layers electrically connected" used herein implies that electrons can move in both the forward direction and the reverse direction through the silicon substrate.

The present embodiment will describe a process for fabricating such a silicon substrate. The process for fabricating the silicon substrate having a plurality of recessed portions each provided with a metal layer on the bottom thereof includes the following steps of (a) to (e):
(a) forming a first insulating layer 20 on a surface of a silicon substrate 1;
(b) forming recessed portions 2 in the silicon substrate 1 by partially removing the first insulating layer 20 to expose the surface of the silicon substrate 1, and etching the silicon substrate 1 from the exposed surface through the first insulating layer 20 as a mask;
(c) forming a second insulating layer 21 on the side walls 7 and bottoms 3 of the recessed portions 2;
(d) removing at least partially the portions of the second insulating layer 21 disposed on the bottoms 3 of the recessed portions 2 to expose the surface of silicon substrate at the bottoms of the recessed portions; and
(e) forming a metal layer 22 on the top surfaces 8 around the recessed portions and the surface of the silicon substrate exposed at the bottoms of the recessed portions in the step of (d).

Figure 3A:
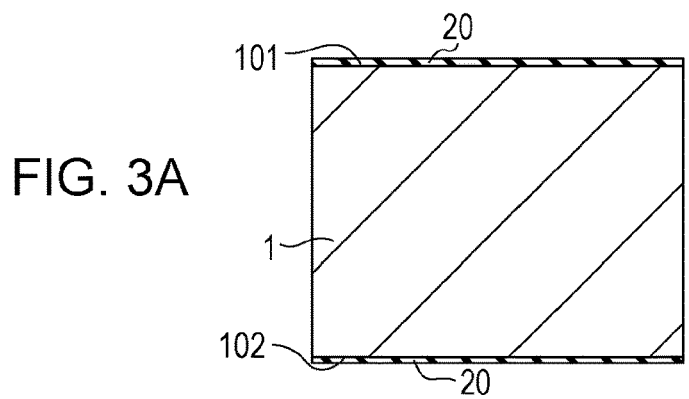
FIGS. 3A to 3G are process diagrams of a method for manufacturing a structure according to a third embodiment of the present disclosure.
Figure 3B:
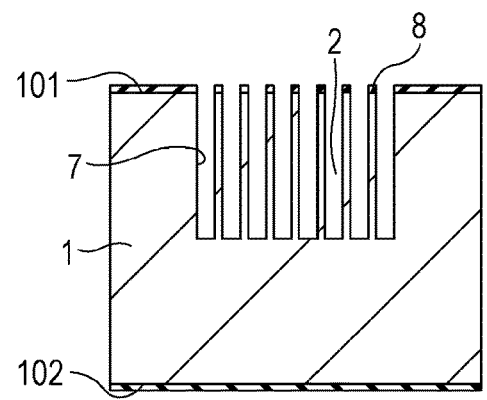

These steps will now be described.
(a) Step of Forming a First Insulating Layer 20 on a Surface of a Silicon Substrate As shown in FIG. 3A, the first insulating layer 20 is formed on a surface of a silicon substrate. The first insulating layer 20 may be made of silicon oxide or silicon nitride. The thickness of the first insulating layer 20 may be in the range of 0.1 μm to 5 μm. For forming a silicon oxide first insulating layer 20, for example, thermal oxidation or chemical vapor deposition (CVD) can be applied. For forming a silicon nitride first insulating layer 20, for example, CVD can be applied. Although in FIG. 3A, both the second surface 101 of the silicon substrate and the third surface 102 thereof opposing the second surface 101 are provided with the insulating layer 20, the insulating layer 20 may be formed only on the second surface 101. It is however advantageous to form the first insulating layer 20 also on the third surface 102. The insulating layer 20 on the third surface 102 can prevent plating metal from growing from the rear surface of the substrate in a subsequent step of electroplating.
(b) Step of Forming Recessed Portions As shown in FIG. 3B, the first insulating layer 20 on the second surface 101 of the silicon substrate 1 is partially removed to form a mask pattern on the second surface 101 simultaneously with partially exposing the second surface 101 of the silicon substrate 1. The case of removing a $SiO_2$ first insulating layer 20 will now be described by way of example of the technique for partially removing the first insulating layer 20 to form the mask pattern. For example, after forming a metal layer, such as a chromium layer, on the first insulating layer 20, a photoresist is applied on the metal layer. Then, the photoresist is subjected to exposure to form a pattern. The shape and dimensions of the pattern are set depending on the pattern and pitch of the intended structure. For a one-dimensional analysis grating of a Talbot interferometer, a pattern including lines at a pitch of 2 μm to 12 μm is suitable. The photoresist pattern is transferred to the metal layer by etching. The etching of the metal layer may be performed by wet etching, or dry etching such as ion sputtering or reactive gas plasma etching. Then, the first insulating layer 20 is etched using the pattered metal layer as a mask. For etching the first insulating layer 20, dry etching may be suitable. For the $SiO_2$ first insulating layer, dray etching using $CHF_3$ plasma is suitable. The metal layer on the first insulating layer 20 may be removed after the completion of the etching of the first insulating layer 20.

Subsequently, the silicon substrate 1 is etched to form a plurality of recessed portions 2 from the exposed surface thereof using the pattern of the first insulating layer 20 as a mask. The etching of the silicon substrate 1 may be performed by wet etching using a solution, or dry etching such as ion sputtering or reactive gas plasma etching. Highly anisotropic dry etching is however more advantageous. Among dry etching techniques, reactive ion etching (RIE) is suitable to form recessed portions having a high aspect ratio. In particular, the Bosch process, in which etching with $SF_6$ gas and deposition of a side wall protecting film with $C_4F_8$ gas are alternately performed, is more suitable as RIE for forming recessed portions having a higher aspect ratio. The aspect ratio of each recessed portion is desirably in the range of 10 to 150. In the case of Bosch process, desirably, the side wall protecting film is removed after RIE. The side wall protecting film may be removed by, for example, oxygen plasma ashing or washing with hydrofluoroether (HFE) solution. The verticality of the recessed portions in the depth direction is set corresponding to the verticality in the depth direction of the recessed portions in the desired structure. Hence, the recessed portions are formed at an angle as described in the first embodiment. It is known that the Bosch process leaves asperities called scallops in the side walls 7 of the recessed portions. If the side walls 7 of the recessed portions have such asperities, in the present disclosure, the asperities are neglected for determining the angle between the side wall 7 and the surface of the substrate. In this instance, the angle between the side wall 7 and the top surface 8 around the recessed portions is defined by the angle between the top surface 8 and an imaginary flat plane through the bottoms of the asperities. The asperities mentioned herein refer to a roughness of about 0.1 μm or less. For forming the protrusion portions of the second embodiment, the angle between the side wall and the surface of the substrate is defined in the same manner as above.

(c) Step of Forming a Second Insulating Layer 21

Figure 3C:
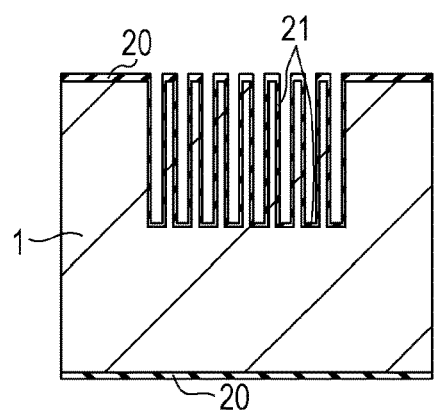

As shown in FIG. 3C, a second insulating layer 21 is formed on the side walls 7 and bottoms 3 of the recessed portions 2 in the silicon substrate 1. The second insulating layer 21 on the side walls 7 of the recessed portions can prevent plating metal from growing from the side walls of the recessed portions during electroplating.

The thickness of the second insulating layer 21 may be in the range of 10 μm or more. A naturally oxidized film is formed over the surface of the silicon substrate even if step (c) is not performed. The naturally oxidized film however has a thickness as small as about 2 nm, and is therefore often insufficient as the insulating layer. The second insulating layer 21 having a thickness of 10 nm or more is more insulating than the naturally oxidized silicon film. Even if the silicon substrate is electrified in a subsequent step, current hardly flow across the surface of the second insulating layer 21. Also, the second insulating layer 21 formed by thermal oxidation of silicon exhibits higher reliability in insulation. The thermal oxidation of silicon, which is a thermal reaction, allows the second insulating layer 21 to be formed on the side walls 7 and bottoms 3 of the recessed portions 2 to a uniform thickness even if the recessed portions 2 have a large aspect ratio. Thus, the second insulating layer 21 can be formed while keeping the verticality of the recessed portions formed in step (b).

Depending on the aspect ratio and pitch of the metal portions in the recessed portions, the current for plating, and the allowance for failure in filling the recessed portions (hereinafter referred to as filling failure), the metal structure may be formed by plating without forming the insulating layer on the side walls of the recessed portions. In such a case, Step (c) may be omitted.

Figure 3D:
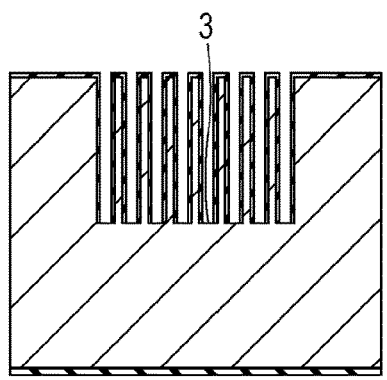

(d) Step of Exposing the Surface of the Silicon Substrate at the Bottoms of the Recessed Portions As shown in FIG. 3D, the portions of the second insulating layer 21 disposed on the bottoms 3 of the recessed portions 21 are, at least in part, removed to expose the surface of the silicon substrate at the bottoms 3 of the recessed portions. After exposing the surface of the silicon substrate at the bottoms of the recessed portions, a metal layer 24 is formed on the surface of the silicon substrate at the bottoms of the recessed portions in Step (e) for forming silicide.

The removal of the second insulating layer 21 may be performed by dry etching using a highly anisotropic first etching gas, but is not limited to such dry etching as long as the recessed portions can maintain the desired verticality and width. For example, the removal may be performed by ion sputtering, reactive gas plasma etching, or argon sputtering. For the second insulating layer 21 of silicon oxide, silicon nitride or silicon nitroxide, suitable is RIE using a reactive gas containing a gas expressed by the general formula $C_xH_yF_z$.

In the general formula, x represents an integer of 1 or more, y represents an integer of 0 or more, and z represents an integer of 1 or more.

Examples of the gas expressed by general formula (1) include $CF_4$, $CHF_3$, $C_2F_6$, $C_3F_8$, and c-$C_4F_8$ (octafluorocyclobutane), and any other $C_xH_yF_z$ gas can be used as long as it is anisotropic reactive ion etching gas that can etch the second insulating layer 21.

Highly anisotropic reactive ion etching allows the second insulating layer 21 on the bottoms 3 of the recessed portions to be more preferentially removed than the second insulating layer 21 on the side walls 7 of the recessed portions. The etching is stopped at the moment when the second insulating layer 21 is, at least in part, removed from the bottoms 3 of the recessed portions to expose the surface of the silicon substrate. In this state, the silicon surface will be brought into direct contact with a metal layer formed in the following step (e) of forming a metal layer, thus forming silicide.

Instead of stopping the etching at the moment of exposing the surface of the silicon substrate, the etching may be continued until the silicon surface is slightly etched. In reactive ion etching, the difference in etching rate at a plane of the silicon substrate between the second insulating layer and the silicon is unlikely to be zero, and the difference increases as the area of the silicon substrate is increased. Consequently, the bottoms 3 of the recessed portions tend to has portions from which the second insulating layer 21 has been removed and portions from which the second insulating layer 21 is not removed. Silicide is unlikely to be formed at the bottoms 3 of the recessed portions at which the silicon surface is not exposed due to the presence of the unremoved second insulating 21, even by the following step of forming a metal layer and heating the metal layer. This is because the remaining second insulating layer 21 interferes with the contact of the silicon surface with the metal layer. In order to remove the second insulating layer 21 completely from the bottoms 3 of the recessed portions at the same surface of the silicon substrate, it is desirable to continue the etching without stopping the etching at the moment of exposing the silicon surface, until the silicon surface is slightly etched (over-etching).

In order to stop etching at the moment when the surface of a silicon substrate having a small area is exposed with the first etching gas, process conditions are strictly controlled, and hence process margin is small.

Accordingly, over-etching is advantageous for etching with the first etching gas rather than stopping the etching at the moment when the silicon surface is exposed. The present inventors however found that the use of the gas containing a reactive gas expressed by $C_xH_yF_z$ as the first etching gas makes it difficult to form silicide even though the metal layer is formed and heated in a subsequent step. The present inventors also found that this is because the etching of silicon with the reactive gas $C_xH_yF_z$ is liable to cause fluorocarbon polymer (reaction product) to be deposited on the silicon surface, and because the fluorocarbon polymer interferes with the contact between the silicon surface and the metal layer.

It is therefore advantageous to remove the fluorocarbon polymer with the second etching gas after the over-etching of the second insulating layer with the first etching gas, if the first etching gas contains the reactive gas $C_xH_yF_z$. Such two-step etching using the first etching gas and the second etching gas enables the silicon surface to be exposed with a process margin ensured.

The second etching may be argon sputter etching, and reactive ion etching gas is advantageous. The second etching gas is such that it can remove fluorocarbon polymer, and does not oxidize silicon into $SiO_2$ or does not form a deposit on the silicon surface. In the use of the second etching gas, the etching selectivity of the second insulating layer on the side walls to the fluorocarbon polymer on the bottoms of the recessed portions (etching rate of the second insulating layer/etching rate of the fluorocarbon polymer) is desirably 1/50 or less. More desirably, the second etching gas has an etching selectivity of 1/100 or less. The second etching gas may contain, but not limited to, sulfur hexafluoride, chlorine, bromine, hydrogen bromide, ammonium trifluoride, silicon tetrafluoride, silicon tetrachloride, chlorine trifluoride, or phosphorus trichloride.

In addition, by forming the first insulating layer 20 on the top surfaces 8 around the recessed portions to a larger thickness than the second insulating layer 21, the second insulating layer 21 can be removed from the bottoms 3 of the recessed portions with the first insulating layer remaining on the top surfaces 8.

For electrifying the silicon substrate for electroplating, it is desirable the portions coming into contact with the plating solution other than the silicide layers be not electrified. It is therefore desirable that the first insulating layer 20 remain with a thickness of 0.1 µm or more on the top surfaces 8, and that the second insulating layer 21 remain with a thickness of 10 nm or more on the side walls 7.

(e) Step of Forming a Metal Layer

Figure 3E:
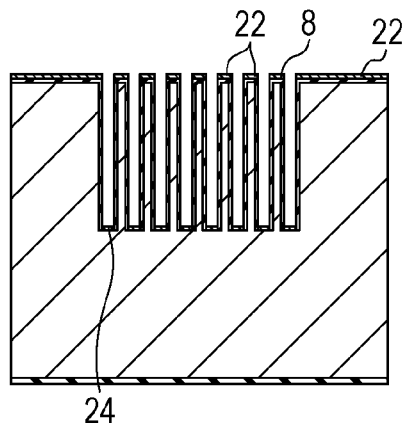

Subsequently, as shown in FIG. 3E, a metal layer 22 is formed on the top surfaces 8 around the recessed portions and a metal layer 24 is formed on the bottoms of the recessed portions. Since the surface of the silicon substrate is exposed at the bottoms of the recessed portions, the metal layer 24 comes into contact with silicon at the bottoms of the recessed portions. On the other hand, on the top surfaces 8 around the recessed portions, the first insulating layer 20 and the metal layer 22 are disposed in that order; hence, the metal layer 22 does not come into contact with the top surface of the silicon substrate. Also, the metal layer 22 over the top surfaces 8 is electrically isolated from the metal layer 24 on the bottoms by the first insulating layer 20 on the top surfaces 8. For forming the metal layers 22 and 24, a highly directive method is advantageous because such a method does not easily allow the metal layer to be formed on the side walls 7 of the recessed portions. Electron beam deposition and resistance heating vapor deposition are examples of the highly directional method. Alternatively, less directional methods, such as vacuum sputtering, ion beam sputtering or CVD, may be applied. Although these less directional methods form the metal layer on the side walls 7 of the recessed portions, the second insulating layer 21 on the side walls 7 of the recessed portions prevents silicon from coming into contact with the metal layer. Silicide is therefore not formed on the side walls 7 even after the below-described step of forming silicide. Silicide can be selectively formed on the bottoms of the recessed portions.

Thus, the silicon substrate having a plurality of recessed portions and a metal layer on the bottoms of the recessed portions is prepared through the steps of (a) to (e).

Figure 3F:
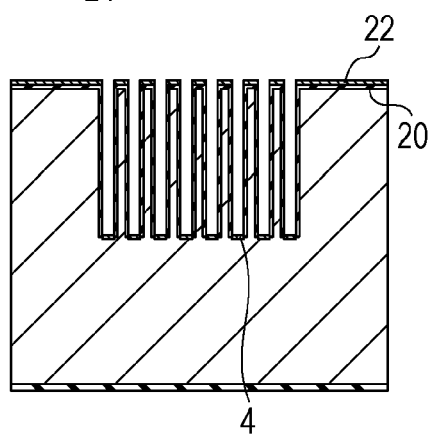

Subsequently, silicide is formed as shown in FIG. 3F by heating the silicon substrate. The heating temperature may be set according to the silicide to be formed (that is, the types of silicon and metal), and is generally in the range of 200° C. to 1000° C. The heating for forming silicide may be performed in any atmosphere. Also, the method for heating is not particularly limited. For example, the silicon substrate may be heated in an oven or on a heater such as a hot plate. Since the silicon surface at the bottoms 3 of the recessed portions is in contact with the metal layer 24, a silicide layer is formed by heating. On the other hand, the silicon surface at the top surfaces 8 around the recessed portions is not in contact with the metal layer 22, silicide is not formed even by heating. Similarly, silicide is not formed on the side walls 7 of the recessed portions even though a metal layer is formed on the side walls 7 of the recessed portions. The second insulating layer 21 prevents the metal layer from coming into contact with the silicon surface.

When the silicon substrate is heated with the metal layer in contact with the bottoms of the recessed portions, as described above, the metal in the metal layer is diffused into the silicon substrate at the bottoms of the recessed portions. Thus, the silicide may define the bottoms of the recessed portions. In the description in this disclosure, when the bottoms are defined by the silicide layer as above, the bottoms of the recessed portions and the silicide layers are considered to be in contact with each other.

(2) Step of Forming Metal Structure 5

Figure 3G:
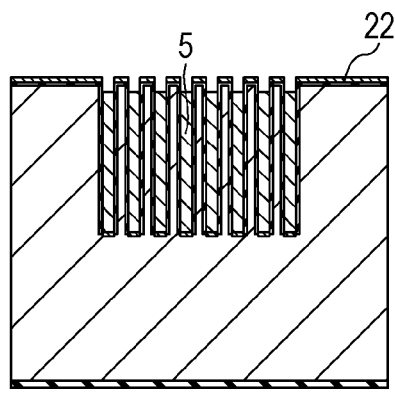

In Step (2), the silicide layers 4 at the bottoms of the recessed portions in the silicon substrate prepared in Step (1) are electrified for electroplating. Thus each recessed portion, at least in part, is filled with a metal, and thus a metal structure 5 is formed as shown in FIG. 3G. Depending on the thickness of the metal layer 24 or the temperature or other conditions for forming the silicide layer 4, a small amount of silicon or silicon oxide can be deposited on the surface of the silicide layer or the surface of the metal layer on the silicide. The silicon or silicon oxide deposited on the surface of the silicide layer or metal layer 24 however does not adhere firmly to the silicide layer or the metal layer 24 and can be easily removed by washing with water. Also, even if silicon oxide or silicon remains between the silicide layers 4 and the metal portions 13 of the metal structure 5, the adhesion between the silicon substrate and the metal structure is higher than the case of the metal structure in contact with silicon without the silicide layer, as long as there is a region where the silicide layer 4 is in contact with the metal portion 13 of the metal structure 5. In the description of the present disclosure, even if silicon or silicon oxide is disposed between the silicide layer 4 and the metal portion 13 of the metal structure 5, the silicide layer 4 and the metal portion 13 of the metal structure 5 are considered to be in contact with each other as long as there is a region where the silicide layer 4 and the metal portion 13 of the metal structure 5 are in contact with each other. In general, silicon is deposited to a thickness of about 5 nm or less on a silicide surface, and silicon oxide is deposited to a thickness of about 5 nm or less. Although silicon oxide is an insulating material, a silicon oxide layer having a thickness as small as 5 nm or less allows electrification of the silicide layer 4 covered therewith for electroplating of the recessed portions. Hence, electroplating may be performed with such deposit remaining. In the description of the present disclosure, the silicide layer 4 and the metal structure 5 are considered to be electrically connected when the silicide layer 4 and the metal structure 5 are electrically isolated from each other to the extent that the insulation there between can be broken down by electroplating. Even when the silicon substrate 1 is monocrystalline, deposited silicon is unlikely to be monocrystalline.

By electrification using the silicon substrate 1 as a cathode and an opposing electroconductive substrate as an anode, the silicide layers 4 are electrified through the silicon substrate 1 for plating using the silicide layers 4 as a seed. Thus, the recessed portions are filled with a metal to form the metal structure 5. Consequently, the structure 10 is completed which includes the metal structure 5 including a plurality of metal portions 13 arranged in the silicon substrate. The resulting structure 10 can be used as an X-ray shield grating. Plating using the silicide layers 4 at the bottoms of the recessed portions as a seed helps a metal fill recessed portions selectively from the bottoms of the recessed portions. Thus, the recessed portions can be filled with a metal even if the recessed portions have a high aspect ratio and high verticality. For filling the recessed portions having a large aspect ratio and high verticality with a metal, it is more effective in reducing voids to grow a plating metal from the bottoms of the recessed portions, in comparison with via-filling plating that is a known method for growing a plating metal from both the side walls and bottoms of the recessed portions.

The space of each recessed portion need not be fully filled with the metal. For example, even when plating is terminated at a point where a metal fills the recessed portions to a half of the height of the recessed portions, the recessed portions are considered to be filled with the metal in the description of the present disclosure. Also, part of the metal layer 24 may remain as it is without being silicidated in Step (1). In this instance, the plating metal is deposited on the surface of the metal layer covering the silicide layer, but not on the surface of the silicide layer. The silicide layer is however considered to be a portion of the seed because the metal layer acting as the seed is electrified through the silicide layer. At this time, the portion of the metal layer 24 remaining without being silicided will act as part of the metal structure.

The structure of the second embodiment can be manufactured basically in the same manner as the structure of the first embodiment. The structure of the second embodiment is however different from the structure of the first embodiment in that the silicon substrate having a plurality of recessed portions and a metal layer on the bottoms of the recessed portions is substituted with a silicon substrate having a plurality of protrusion portions on a first surface and a metal layer in regions of the first surface between the protrusion portions. In this structure, the metal structure 5 has a plurality of holes corresponding to the protrusion portions and the metal portions 13 thereof one each lie on the silicide layers. The silicon substrate used for manufacturing the structure of the second embodiment can be prepared basically through the same steps as the above-described steps of (a) to (e). Step (b) of pattering the first insulating layer is however different from the manufacturing method for the structure of the first embodiment. More specifically, the first insulating layer is patterned so that the first insulating layer remains corresponding to the plurality of protrusion portions, and thus the protrusion portions remain as the top view shown in FIG. 2C.

Fourth Embodiment

A method for manufacturing the structural bodies according to the first and second embodiments will now be described in detail. The method for manufacturing the structure 10 according to the present embodiment is different from the method of the third embodiment in that a step is performed between Steps (1) and (2) of the third embodiment. In this step, the metal layer 22 formed on the first insulating layer 20 on the top surfaces 8 around the recessed portions is removed to expose the first insulating layer 20. In the case of manufacturing the structure of the second embodiment, a step is performed between Steps (1) and (2). In this step, the metal layer 22 formed on the first insulating layer 20 on the top surfaces 18 of the protrusion portions is removed to expose the first insulating layer. In the following description, both the metal layers disposed on the first insulating layer on the top surfaces 8 around the recessed portions or the top surfaces 18 of the protrusion portions may be collectively referred to as the top metal layer. Although the method for manufacturing the structure of the first embodiment will now be described in detail by way of example, Step (1) of forming the silicide layers and Step (2) of forming the metal structure are the same as in the third embodiment and thus description thereof is omitted.

In the present embodiment, after the silicide layers 4 are formed on the bottoms of the recessed portions in Step (1), the top metal layer 22 is removed to expose the insulating layer 20. If the metal layer is disposed on the side walls 7 of the recessed portions with the second insulating layer 21 therebetween, the metal layer is removed simultaneously with the top metal layer by non-anisotropic etching. The metal layer 22 may be removed by any method, and, for example, by being immersed in an etchant for the metal forming the metal layer 22. For this operation, the etchant is such that it can selectively etch the metal layer, but not silicide. The etchant capable of selectively etching the metal layer but not silicide refers to an etchant that etches silicide at an etching rate of 1/100 or less of the etching rate of the metal layer. This removal of the metal layer 22 also removes unsilicidated portions of the metal layer 24 from the bottoms of the recessed portions, but leaves the silicide layers 4 without etching. The remaining silicide layers 4 are used as a seed in the following Step (2).

Figure 6A:
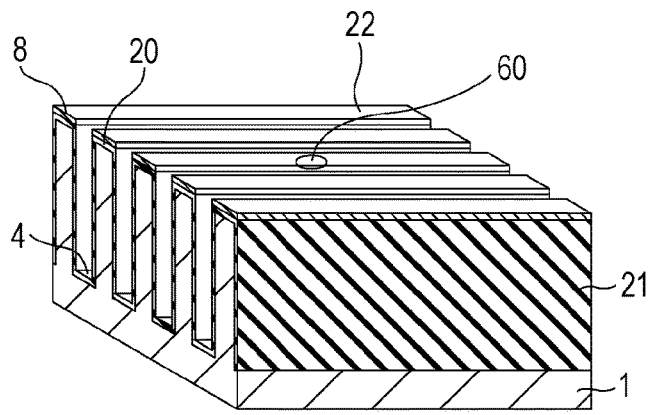
FIGS. 6A to 6D are representations illustrating the effect of a fourth embodiment.
Figure 6B:
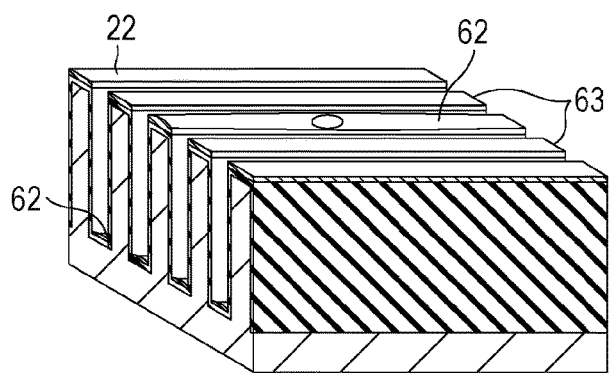
Figure 6C:
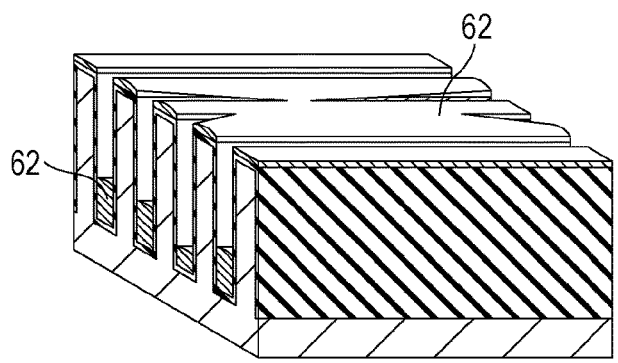
Figure 6D:
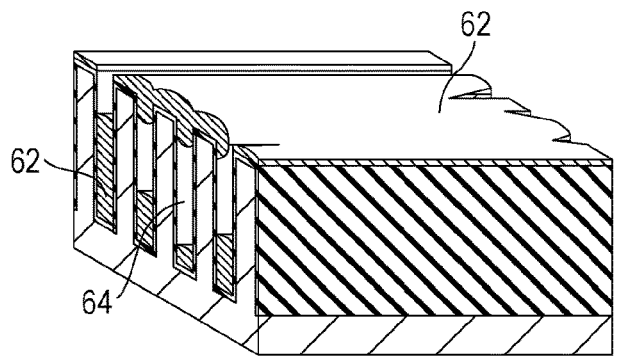

By removing the top metal layer to expose the first insulating layer 20 before Step (2), plating metal is prevented from growing from the metal layer of all the top surfaces even if the insulation between the top metal layer and the silicon substrate is insufficient. For example, the first insulating layer 20 on the top surfaces 8 may have a pinhole due to particulate matter deposited on the silicon surface during Step (1). If a pinhole is formed in the first insulating layer 20, the portion 60 of the top metal layer 22 right above the pinhole is in contact with the corresponding top surface 8 (FIG. 6A). Therefore the entirety of the top metal layer 22 is electrified through the pinhole in the first insulating layer when plating is performed using the silicon substrate 1 as a cathode, and the plating metal 62 is deposited around the portion 60 of the top metal layer right above the pinhole (FIG. 6B). The deposited metal 62 is grown by further plating and is connected to the adjacent portions 63 of the top metal layer 22 separated by the recessed portions 2. Consequently, the adjacent portions 63 are also electrified, and from which the metal 62 is grown by plating (FIG. 6C). If the grown metal 62 is further grown by plating to the extent that the entries of the recessed portions are closed with the metal, the plating solution cannot enter the recessed portions and voids 64 are formed (FIG. 6D).

If the silicon substrate 1 is electrified for electroplating in spite of insufficient insulation of the first insulating layer on the top surfaces, the current flows to the top metal layer 22 through the silicon substrate 1. Thus the plating metal may fail to fill the recessed portions satisfactorily. Particularly in the case of the recessed portions arranged in lines as in the first embodiment, the metal layer 22 is formed in a manner of lines on the top surfaces. Accordingly, the metal 62 extends in lines from the top surfaces, thus failing, in a plane manner, to fill the recessed portions (FIG. 6D).

FIG. 8A is a schematic representation illustrating the formation of a metal layer by highly directional electron beam deposition. If a metal layer is deposited on a silicon substrate 1 having recessed portions 2 in a larger area relative to the deposition source 70, the metal layers 22 and 24 are deposited only on the top surfaces 8 and bottoms 3, respectively, in the middle portion of the substrate right above the deposition source 70. As the distance between the deposition source and the middle portion of the substrate is increased, the directions of deposition deviate more from the depth direction of the recessed portions 2, and the deposit hits the silicon between the recessed portions. Thus the metal layer 23 becomes likely to be deposited on the side walls 7. The metal layer 23 on the side walls 7 thus becomes likely to connect to the metal layer 24 on the bottoms of the recessed portions. Consequently, the metal layer 23 is electrically connected to the silicide layers after silicide is formed. If the silicon substrate 1 in this state is electrified for electroplating, the current flows to the metal layer 23 on the side walls 7 through the silicon substrate 1, and the plating metal is deposited and grown from the side walls 7. Thus the plating metal becomes liable to fail to fill the recessed portions satisfactorily. It is therefore desirable to remove the metal layer 23 after the silicide layers have been formed. In order to remove the metal layer 23, the silicide layers are formed in a state where the side walls 7 and the metal layer 23 are separate from each other, and the metal layer 23 is subjected to etching so as to selectively etch the metal layer 23 but not the silicide layers. Since the side walls 7 are covered with the second insulating layer 21, the side walls 7 and the metal layer 23 are not brought into contact with each other after the silicide layer is formed in the same manner as in the third embodiment. Non-anisotropic etching such as wet etching enables the metal layer 23 on the side walls 7 to be removed simultaneously with the top metal layer 22.

This prevents the plating metal from being deposited and grown from the side walls and reduces the failure in filling the recessed portions with a metal. Also, even if the top metal layer 22 and the metal layer 24 on the bottoms of the recessed portions are electrically connected through the metal layer 23 on the side walls 7, the failure in filling the recessed portions can be reduced by removing the metal layers 22 and 23 from the tops or the side walls after the formation of the silicide layer 4.

Figure 8B:
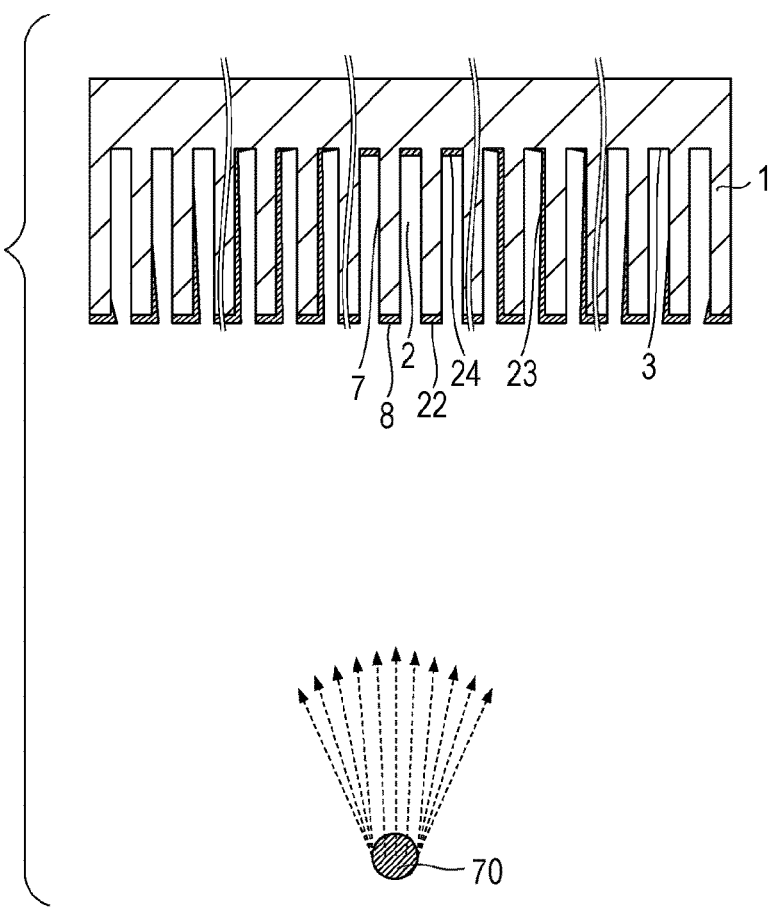
Figure 8C:
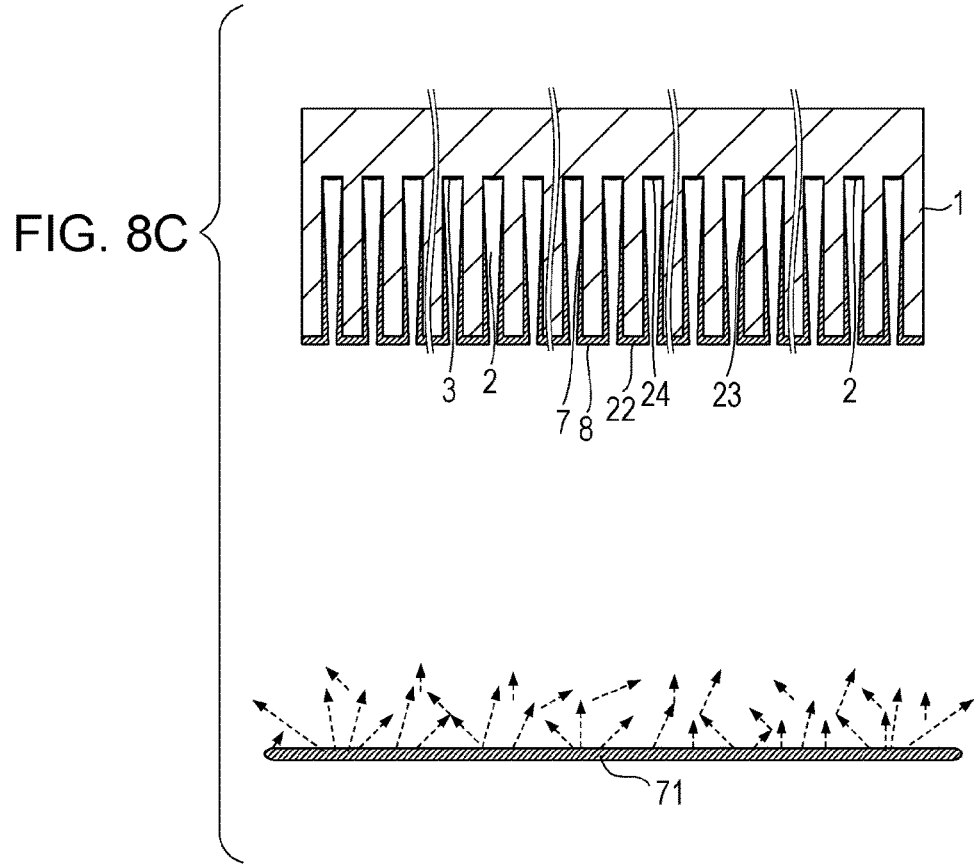

FIG. 8B is a schematic representation illustrating the formation of a metal layer on a silicon substrate 1 having recessed portions in a larger area than the case of FIG. 8A by electron beam deposition. As the distance between the deposition source and the middle portion of the substrate is increased, the directions of deposition deviates more from the depth direction of the recessed portions 2. Thus the silicon between the recessed portions 2 blocks the metal of the metal layer and hinders the metal layer from being formed on the bottoms 3 of the recessed portions 2. Thus, a less directional method is applied to form a metal layer in a large area. FIG. 8C is a schematic representation illustrating the formation of a metal layer by vacuum sputtering. By using a sputtering target 71 having a large diameter, the metal layer 24 can be easily formed on the bottoms 3 of the recessed portions 2, and also the metal layer 23 becomes liable to be formed on the side walls 7. In this instance, the deposition of the plating metal on the side walls can be reduced by removing the metal layer 23 after the formation of the silicide layers 4, as in the above case.

By removing the metal layer 22 from the top surfaces to expose the first insulating layer 20 before Step (2) of electroplating, as in the present embodiment, and then performing electroplating with the first insulating layer exposed, failure in filling recessed portions can be reduced. Even if a pinhole is formed in the first insulating layer 20, only the silicon surface exposed in the pinhole is electrified as long as the first insulating layer is exposed. Metal deposition thus can be occur more locally than the case where the metal layer 22 is disposed on the top surfaces, and accordingly the failure in filling recessed portions is more unlikely to occur. Similarly, even if a pinhole is formed in the second insulating layer 21 on the side walls, voids can be reduced by removing the metal layer 23 from the side walls not provided with the silicide layer. Even though a metal layer is formed except for the bottoms of the recessed portions, the metal layer can be removed after the formation of the silicide layer 4. Thus, voids resulting from pinholes and problems or defects in the metal structure 5 can be reduced.

Although the third and fourth embodiments have described exemplary methods for manufacturing the structural bodies of the first and second embodiments, the method of the present invention is not limited to the disclosed embodiments. For example, the metal portions of the metal structure may be formed in the recessed portions by sputtering instead of electroplating. In this instance, the silicide layer may be formed on a metal layer that has been formed on the top surfaces 8 exposed. In the case of electroplating, also, metal deposition on the top surfaces can be prevented by forming a silicide layer on the top surfaces, and then forming an insulating layer so as to cover the top surfaces by oblique vapor deposition. As an alternative to the first insulating layer, an electroconductive protective layer may be formed on the top surfaces, and the metal layers 22 and 24 are formed on the protective layer and the recessed portions, respectively. Then, after the silicide layer 4 is formed on the bottoms of the recessed portions, the metal layer and the protective layer are removed from the top surfaces, and an insulating layer is formed on the top surfaces before electroplating. Even if the metal layer is disposed in contact with the silicon of the top surfaces, the silicide layer 4 can be selectively formed at the bottoms of recessed portions by heating after the metal layer is removed by electrolytic etching as disclosed in Japanese Patent Laid-Open No. 2013-178361. If the side walls of the recessed portions (in the case of the first embodiment) or the protrusion portions (in the case of the second embodiment) are formed by using a photosensitive resist, silicide is not formed even if the resist is in contact with a metal. Therefore the silicide layer can be formed only at the bottoms of the recessed portions even if the metal layer is formed on the top surfaces where silicon is exposed.

Fifth Embodiment

The present embodiment will describe a Talbot interferometer 50 including the structural bodies of the first embodiment as a source grating 54 and an analysis grating 59.

Figure 5:
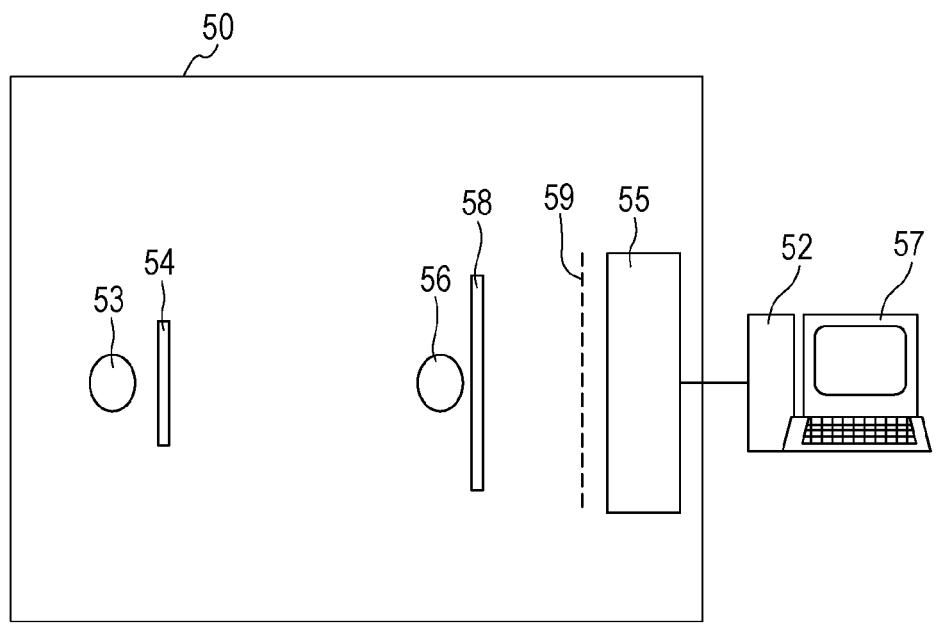
FIG. 5 is a schematic view of a Talbot interferometer according to a fifth embodiment of the present disclosure.

The X-ray Talbot interferometer 50 of the present embodiment is schematically shown in FIG. 5. The X-ray Talbot interferometer 50 is an X-ray Talbot-Lau interferometer including a source grating 54. The X-ray Talbot interferometer 50 includes an X-ray source 53, the source grating 54 capable of dividing X-ray radiation from the X-ray source 53 to form a virtual arrangement of minute X-ray sources, and an X-ray diffraction grating 58 capable of diffracting the X-ray radiation from the source grating 54 to form an interference pattern. The structure of the first embodiment is used as the source grating 54. The X-ray Talbot interferometer 50 also includes an analysis grating 59 capable of partially blocking the X-ray radiation forming the interference pattern to form an X-ray intensity pattern, and an X-ray detector 55 capable of detect the intensity distribution of the X-ray radiation from the analysis grating 59. The analysis grating 59 is also the structure of the first embodiment. The X-ray Talbot interferometer 50 constitutes an X-ray Talbot interferometer system 51 together with an arithmetic device 52 capable of calculating the information of the subject 56 using the detection result of the X-ray detector 55 and a visualize device 57 capable of showing calculation results. The arithmetic device 52 is a computer including a processor, a memory device, a storage device and an input/output device. Hardware such as a logic circuit may be substituted for some of the functions of the arithmetic device 52. The visualize device 57 may be a display device or a printer.

The X-ray Talbot interferometer 50 does not necessarily include the X-ray source 53. If an X-ray Talbot interferometer 50 not having an X-ray source 53 is used for imaging, the x-ray Talbot interferometer 50 may be combined with an X-ray source 53 suitable for imaging.

The structure of the first embodiment may be used as either of the X-ray source grating or the analysis grating. The structure of the second embodiment may be substituted for the structure of the first embodiment.

The present application will be further described in detail with reference to specific examples.

Example 1

Example 1 illustrates a specific method according to the fourth embodiment for manufacturing the structure of the first embodiment with reference to FIGS. 3A to 3F and 4A to 4D.

Step (1) of forming the silicide layers 4 will first be described. In the present Example, a silicon substrate is prepared through Steps (a) to (e) of the third embodiment. These steps will now be described.

A starting silicon substrate 1 is used which has a diameter of 100 mm, a thickness of 200 µm and a resistivity of 0.02 Ωcm. The starting silicon substrate 1 is thermally oxidized at 1050° C. for 4 hours to form an about 1.0 µm thick thermally oxidized film (first insulating layer 20) on the second surface 101 and the third surface 102 of the starting silicon substrate 1 (FIG. 3A).

A positive resist is applied onto the thermally oxidized film on the second surface, and is then subjected to semiconductor photolithography so as to form a resist pattern having openings of 4 µm in width arranged at a pitch of 8 µm in four 20 mm×20 mm regions. Thus resist openings, each a linear opening having a width of 4 µm, are one-dimensionally arranged at a pitch of 8 µm in a striped manner. Then, the thermally oxidized film is subjected to reactive etching with $CHF_3$ to partially expose the surface of the starting silicon substrate 1. Subsequently, the exposed silicon is subjected to anisotropic deep etching by ICP-RIE to form a plurality of recessed portions (FIG. 3B). This etching is performed up to a depth of about 125 µm and then stopped. Thus a plurality of 125 µm deep recessed portions 2 are formed in the starting silicon substrate 1. Each recessed portion has an aspect ratio of 125/4 (=about 31). Subsequently, the resist is removed by UV ozone ashing. Furthermore, the silicon substrate is washed with hydrofluoroether and then a mixture of sulfuric acid and hydrogen peroxide. After being washed with water, the silicon substrate 1 is soaked with isopropyl alcohol and dried.

Then, the side walls 7 and bottoms 3 of the recessed portions formed by the etching are thermally oxidized at 1050° C. for 7 minutes to form an about 0.1 µm thick thermally oxidized film (second insulating layer 21) (FIG. 3C).

Then, the thermally oxidized film is removed from the bottoms of the recessed portions to expose silicon at the bottoms (FIG. 3D). This partial removal of the thermally oxidized film is performed by dry etching using $CHF_3$ plasma. This etching is highly anisotropic and proceeds in a direction substantially perpendicular to the substrate. The insulating layer of the side walls 7 of the recessed portions can therefore be left so as not to expose the silicon at the side walls 7 even though the thermally oxidized film of each bottom is completely removed.

Then, gold is deposited to a thickness of 50 nm in an electron beam deposition apparatus. Thus a gold metal layer 24 is formed on the bottoms 3 of the recessed portions at which the silicon is exposed. At the same time, a gold metal layer 22 is formed on the top surfaces 8 around the recessed portions (FIG. 3E).

Then, the resulting silicon substrate 1 is placed on a hot plate and heated from room temperature. When the temperature of the hot plate has reached 330° C., the silicon substrate 1 is removed from the hot plate. The gold on silicon and the silicon thus form silicide, and the interfaces between the silicon at bottoms of the recessed portions and the metal layer 24 are silicidated into silicide layers 4 (FIG. 3F). On the other hand, the metal layer 22 over the top surfaces does not form silicide because of the presence of the thermally oxidized film on the top surfaces.

Figure 4A:
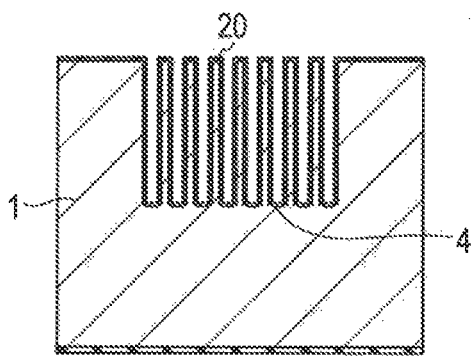
FIGS. 4A to 4D are process diagrams of a method for manufacturing a structure of Example 1.

The resulting silicon substrate shown in FIG. 3F is immersed in an etchant for gold, which is an aqueous solution containing iodine and potassium iodide. Consequently, the gold metal layer 22 is removed by etching, while the silicide layer 4 is left without being etched. The metal layer 22 on the top surfaces 8 is removed to expose the surface of the thermally oxidized film, while the silicide layer 4 is left at the bottoms of the recessed portions (FIG. 4A).

Figure 4B:
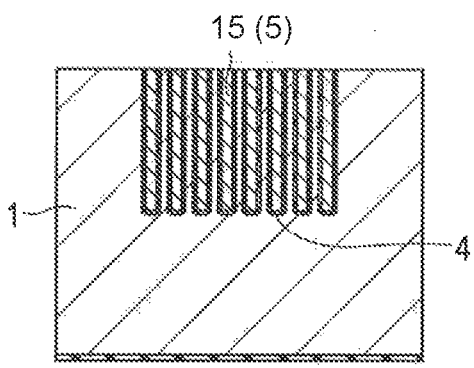

After being washed with water, the silicon substrate 1 is connected to a cathode, and thus subjected to gold plating with a platinum-coated titanium mesh connected to an anode. This gold plating is performed at a current density of 0.2 A/dm$^2$ using a cyan-free gold plating solution Microfab Au 1101 (produced by Nippon Electroplating Engineers) of 60° C. in temperature. A gold plating layer 15 is thus grown from the silicide layers acting as a seed. The gold plating layer 15 is grown until protruding from the recessed portions, and the protruding gold portions are removed by chemical mechanical polishing (CMP) of the gold. At this time, the thermally oxidized film 20 on the top surfaces is simultaneously removed to expose silicon (FIG. 4B).

Figure 4C:
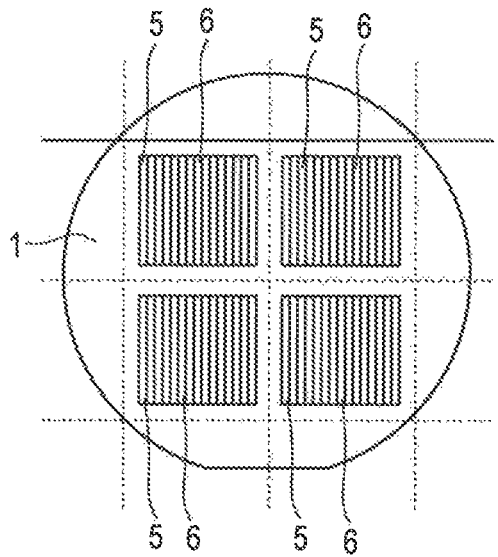
Figure 4D:
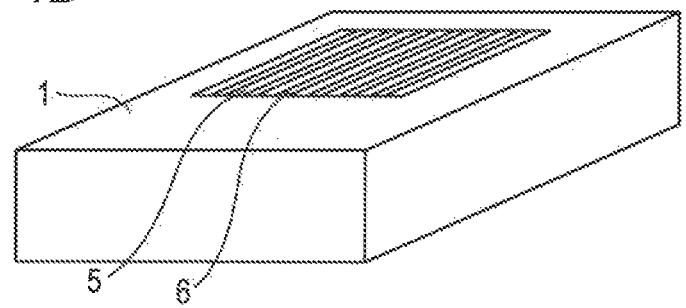

Subsequently, the resulting silicon substrate 1 is diced, as shown in FIG. 4C, into chips of the structure as shown in FIG. 4D. The resulting chips are subjected to ultrasonic cleaning in acetone for removing CMP slurry and shavings or the like of dicing. The gold plating layer 15 in the recessed portions is not removed by nitrogen blowing for drying after ultrasonic cleaning.

In examination through an X-ray microscope, clear high contrast image of the grating was obtained, and defects were not observed in the metal structure. It is thus confirmed that a structure has been obtained which includes a gold metal structure including gold metal portions disposed in recessed portions in a silicon substrate.

Example 2

Example 2 illustrates a method according to the fourth embodiment for manufacturing the structure of the second embodiment with reference to FIG. 2A and FIGS. 7A to 7H. The present Example is different from Example 1 in the mask pattern used for etching the silicon substrate and the material of the metal layer.

Step (1) of forming the silicide layer 4 will first be described. In the present Example, a silicon substrate is prepared through Steps (a) to (e) of the third embodiment. These steps will now be described.

Figure 7A:
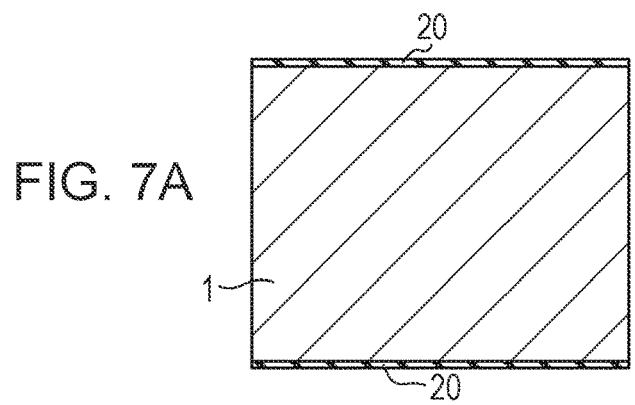
FIGS. 7A to 7H are process diagrams of a method for manufacturing a structure of Example 2.

First insulating layers 20 are formed on the starting silicon substrate 1 in the same manner as in Example 1 (FIG. 7A).

Figure 7B:
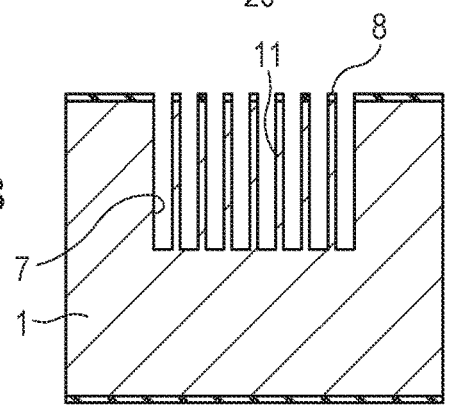

A positive resist is applied onto the first insulating layer 20 on the second surface, and is then subjected to semiconductor photolithography so as to form a resist pattern having circular portions of 4 μm in diameter arranged at a pitch of 8 μm in four 60 mm×60 mm regions. Thus a resist pattern is formed in which 4 μm circular portions are arranged at a pitch of 8 μm. Then, a plurality of protrusion portions 11 are formed by reactive etching with CHF$_3$ and ICP-RIE in the same manner as in Example 1 (FIG. 7B). This etching is performed up to a depth of about 125 μm and then stopped. Thus a plurality of 125 μm high protrusion portions 11 are formed in the starting silicon substrate 1. Each protrusion portion has an aspect ratio of 125/4 (=about 31). The resulting silicon substrate 1 is subjected to resist removal, washing and drying in the same manner as in Example 1.

Figure 7C:
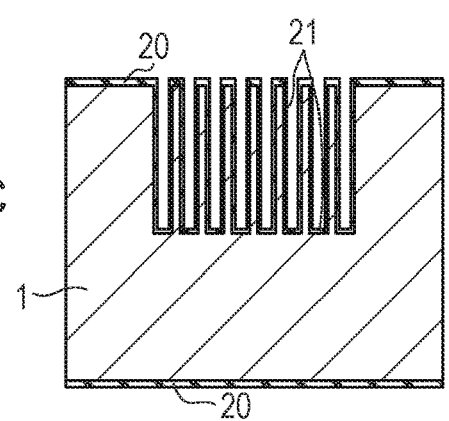

Then, an about 0.1 μm thick thermally oxidized film (second insulating layer 21) is formed on the side walls 7 of the plurality of protrusion portions 11 and on the first surface between the plurality of protrusion portions 11 by the same thermal oxidation as in Example 1 (FIG. 7C).

Figure 7D:
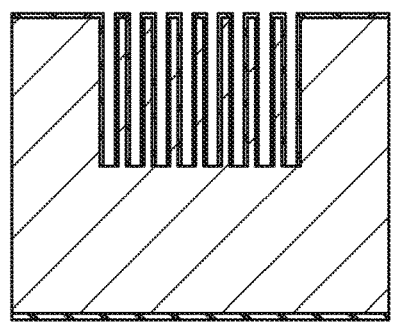

Subsequently, the thermally oxidized film being the second insulating layer is removed from the first surface to expose silicon at the first surface between the plurality of protrusion portions 11 by dry etching using CHF$_3$ plasma in the same manner as in Example 1 (FIG. 7D).

Figure 7E:
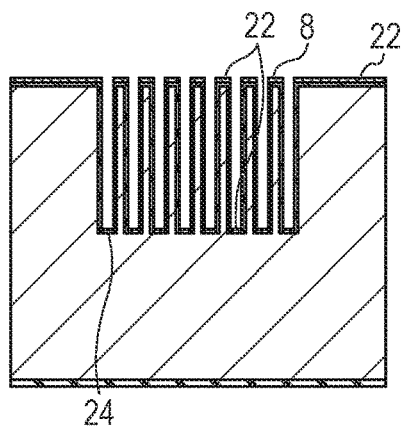

Then, nickel is deposited to a thickness of 50 nm by resistance heating vapor deposition. Thus a nickel metal layer 24 is formed on the silicon surface exposed at the first surface (FIG. 7E). At the same time, a nickel metal layer 22 is formed over the top surfaces 8.

Then, the resulting silicon substrate 1 is placed on a hot plate and heated from room temperature. When the temperature of the hot plate has reached 225° C., the silicon substrate 1 is removed from the hot plate. The nickel on silicon and the silicon thus form silicide, and the interfaces between the nickel metal layer 24 and the silicon between the plurality of protrusion portions 11 are silicidated into silicide layers 4 (FIG. 7F).

Figure 7F:
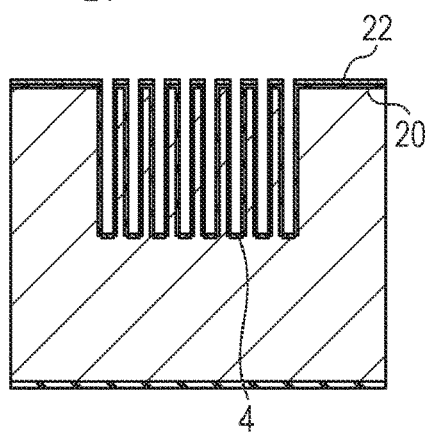
Figure 7G:
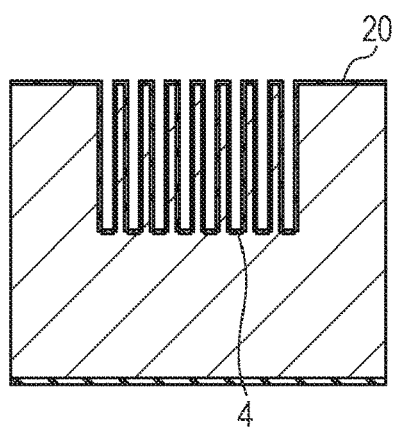
Figure 7H:
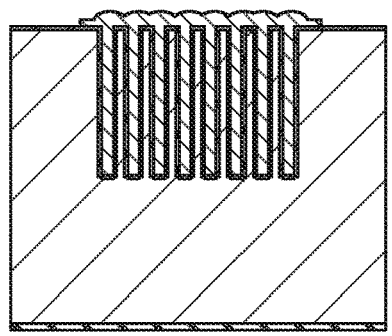

The resulting silicon substrate 1 shown in FIG. 7F is immersed in an etchant for nickel, which is an aqueous solution containing ammonium persulfate and nitric acid. The nickel metal layer 22 on the top surfaces 8 is removed to expose the surface of the thermally oxidized film, while the silicide layer 4 is left in the regions between the plurality of protrusion portions 11 (FIG. 7G).

After being washed with water, the silicon substrate 1 is subjected to electroplating in the same manner as in Example 1. A gold plating layer 15 is grown until protruding from the spaces between the plurality of protrusion portions 11 (FIG. 7H), and the protruding gold portions are removed by CMP of the gold. At this time, the first insulating layer 20 on the top surfaces is simultaneously removed to expose silicon (FIG. 2A). The resulting silicon substrate 1 is subjected to ultrasonic cleaning in the same manner as in Example 1 for removing CMP slurry. The gold plating layer 15 filling the spaces between the protrusion portions is not removed by nitrogen blowing for drying after ultrasonic cleaning.

Example 3

Example 3 illustrates a method according to the fourth embodiment for manufacturing the structure of the second embodiment. The method of the present Example is different from Example 2 in that the plurality of protrusion portions 11 are formed on the silicon substrate 1, using a photosensitive resist.

The starting silicon substrate 1 is the same as that of Example 2. A negative resist SU-8 (produced by Kayaku MicroChem) is applied to the first surface of the starting silicon substrate 1 so as to form a 22 μm thick photosensitive resist layer, followed by soft backing at 95° C. for 10 minutes. Subsequently, the photosensitive resist layer is exposed through a photo mask, using a mask aligner MPA 600 (product name, manufactured by CANON KABUSHIKI KAISHA) including a UV light source. After the exposure, a latent image of a pattern in which squares 2 μm on a side are arranged at a pitch of 4 μm in a two-dimensional manner is formed on the photosensitive resist layer by baking at 65° C. for 5 minutes. Then the latent image is developed with SU-8 developer (produced by Kayaku MicroChem). Unexposed portions of the photosensitive resist layer is dissolved in the developer, and thus 22 μm high protrusion portions of a photosensitive resin are formed in a pattern in which squares 2 μm on a side are two-dimensionally arranged at a pitch of 4 μm. After the development, the resulting silicon substrate 1 is rinsed with isopropyl alcohol and dried. The photosensitive resist layer is thermally cured by being heated at 200° C. for 1 hour. Thus protrusion portions of the photosensitive resist are formed on the first surface of the silicon substrate.

Subsequently, the silicon substrate 1 is washed with an aqueous solution of buffered hydrofluoric acid, and then rinsed with water, followed by drying. Then, nickel is deposited to a thickness of 50 nm by resistance heating vapor deposition. Thus a nickel metal layer 22 or 24 is formed on the silicon exposed between the plurality of protrusion portions 11. At the same time, the nickel metal layer 22 or 24 is also formed on the top surfaces.

Then, the resulting silicon substrate 1 is placed on a hot plate and heated from room temperature. When the temperature of the hot plate has reached 225° C., the silicon substrate 1 is removed from the hot plate. The nickel on the silicon between the plurality of protrusion portions 11 and the silicon thus form silicide, and thus a silicide layer 4 is formed between the plurality of protrusion portions 11. On the other hand, the nickel metal layer 22 over the top surfaces 8 does not form silicide because of the presence of the photosensitive resist layer between the nickel metal layer 22 and silicon.

The silicon substrate 1 is immersed in an etchant for nickel, which is an aqueous solution containing ammonium persulfate and nitric acid. The nickel metal layer 22 is removed by etching, while the silicide layer 4 is not etched. Thus, the nickel metal layer 22 over the top surfaces 8 is removed to expose the surface of the photosensitive resist layer, while the silicide layer 4 is left at the first surface between the plurality of protrusion portions 11. If an insulating photosensitive resist is used, the silicide layer 4 is electrically isolated from the nickel metal layer 22 over the top surfaces 8. Metal is therefore not deposited on the top surfaces 8 by electroplating even though the nickel metal layer 22 is not removed from the top surfaces 8. Thus the step of removing the nickel metal layer 22 from the top surfaces 8 may be omitted.

After being washed with water, the silicon substrate 1 is subjected to electroplating in the same manner as in Example 1. A gold plating layer 15 is thus grown from the silicide layers 4 acting as a seed. The electroplating is stopped when the gold plating layer 15 has reached a thickness of 20 μm. Thus formed gold plating layer 15 filling the spaces between the plurality of protrusion portions 11 is not removed by nitrogen blowing for drying after ultrasonic cleaning.

Example 4

Example 4 illustrates a specific method according to the fourth embodiment for manufacturing the structure of the first embodiment with reference to FIGS. 9A to 9I. A large difference from Example 1 is that the etching of the thermally oxidized film at the bottoms of the recessed portions is continued for a while even after the thermally oxidized film has been removed from the bottoms, thereby removing fluorocarbon polymer formed at the bottoms with a gas containing sulfur fluoride.

Figure 9A:
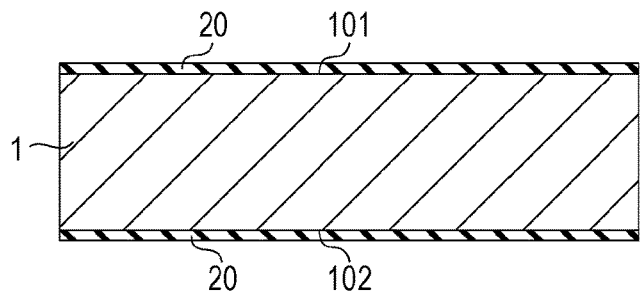
FIGS. 9A to 9I are process diagrams of a method for manufacturing a structure of Example 4.

The starting silicon substrate 1 used in the present Example is a p-type semiconductor silicon substrate having a diameter of 200 mm, a thickness of 500 μm and a resistivity of 0.02 Ωcm. The starting silicon substrate 1 is thermally oxidized at 1050° C. for 4 hours to form an about 1.0 μm thick thermally oxidized film (first insulating layer 20) on the second surface 101 and the third surface 102 of the starting silicon substrate 1 (FIG. 9A).

Figure 9B:
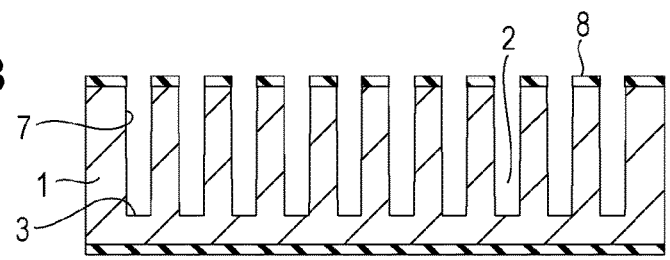

A positive resist (not shown) is applied onto the thermally oxidized film on the second surface, and is then subjected to semiconductor photolithography so as to form a resist pattern having openings of 1.8 μm in width arranged at a pitch of 4 μm in four 130 mm×130 mm regions. Thus resist openings, each a linear opening having a width of 1.8 μm, are one-dimensionally arranged at a pitch of 4 μm in a striped manner. Then, the thermally oxidized film is subjected to reactive etching with $CF_4$ to partially expose the surface of the silicon substrate 1. Subsequently, the exposed silicon is subjected to anisotropic deep etching by ICP-RIE to form a plurality of recessed portions 2 (FIG. 9B). This etching is performed up to a depth of about 100 μm and then stopped. Thus a plurality of 100 μm deep recessed portions 2 are formed in the starting silicon substrate 1. The width of each recessed portion is 1.85 μm in the same plane as the top surfaces 8 and 2.05 μm at the bottoms of the recessed portion 2. The verticality in the depth direction of the recessed portion (angle between the side wall and the top surface) is 90.1 degrees. Each recessed portion has an aspect ratio of 100/1.85 (=about 54).

Subsequently, the resist is removed by UV ozone ashing, and then the silicon substrate is washed with hydrofluoroether and then a mixture of sulfuric acid and hydrogen peroxide, in the same manner as in Example 1. After being washed with water, the silicon substrate 1 is soaked with isopropyl alcohol and dried.

Figure 9C:
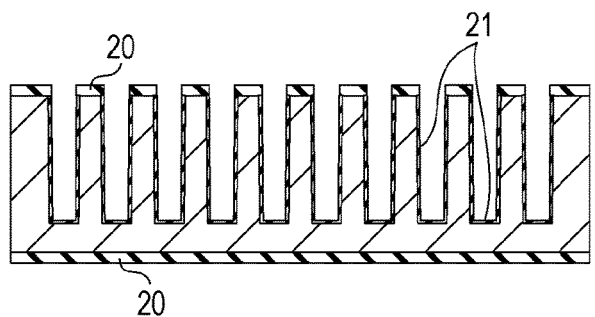

Then, the side walls 7 and bottoms 3 of the recessed portions formed by the etching are thermally oxidized at 1050° C. for 7 minutes to form an about 0.1 μm thick thermally oxidized film (second insulating layer 21) (FIG. 9C).

Figure 9D:
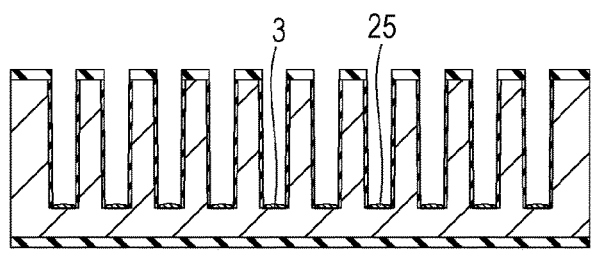

Then, the thermally oxidized film is removed from the bottoms 3 of the recessed portions 2 to expose silicon at the bottoms 3. This partial removal of the thermally oxidized film is performed by dry etching using $CF_4$ as the first etching gas. Etching is continued for another 10 seconds from the moment when a portion of the silicon has been exposed in a region of the recessed portions 2 where the thermally oxidized film has been etched fastest. Consequently, the silicon substrate is etched to a depth of 0 to 0.01 μm from the surface thereof, and fluorocarbon polymer 25 is deposited on the surfaces of the bottoms 3 of the recessed portions 2 (FIG. 9D).

Figure 9E:
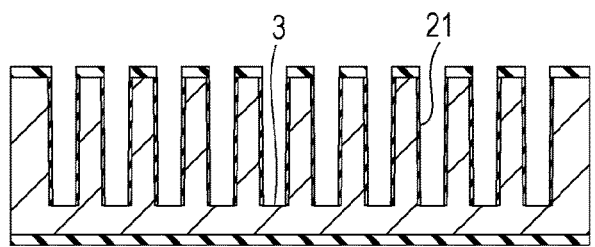

Subsequently, the fluorocarbon polymer 25 deposited on the surface of the silicon substrate is removed by dry etching using sulfur hexafluoride (SFO as the second etching gas to expose the silicon surface at the bottoms 3 of the recessed portions 2 (FIG. 9E). In this operation, the verticality of the recessed portions 2 in the depth direction is kept 90.1 degrees.

Figure 9F:
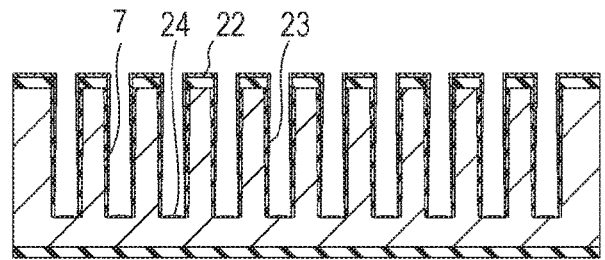

Subsequently, gold is deposited to a thickness of 50 nm in a vacuum sputtering apparatus provided with a sputtering target of 200 mm in diameter. Thus a gold metal layer 24 is formed on the bottoms 3 of the recessed portions 2. At the same time, a gold metal layer 22 is formed on the top surfaces 8, and a metal layer 23 is also formed on the side walls 7 (FIG. 9F).

Figure 9G:
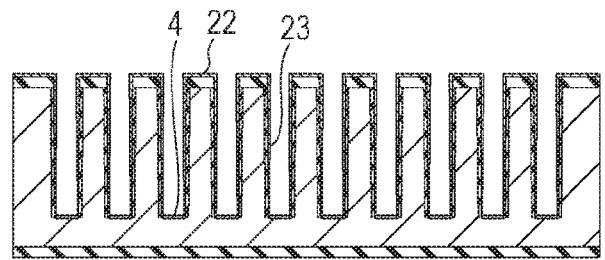

Subsequently, a silicide layer 4 is formed at the bottoms 3 of the recessed portions 2 using a hot plate in the same manner as in Example 1 (FIG. 9G). On the other hand, the metal layers 22 and 23 do not form silicide because of the presence of the thermally oxidized film between the silicon and the metal layer.

Figure 9H:
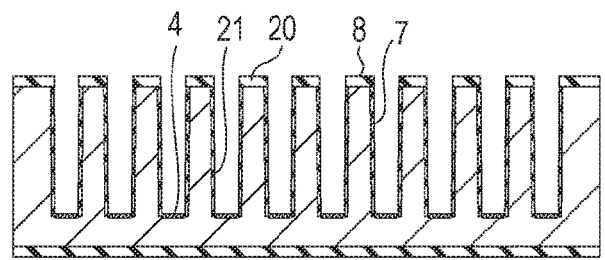

The resulting silicon substrate 1 shown in FIG. 9G is immersed in an etchant for gold, which is an aqueous solution containing iodine and potassium iodide. Thus, the metal layers 22 and 23 are removed in the same manner as in Example 1. Thus the surfaces of the thermally oxidized films on the top surfaces 8 and the side walls 7 are exposed, while the silicide layer 4 is left at the bottoms 3 of the recessed portions 2 (FIG. 9H).

Figure 9I:
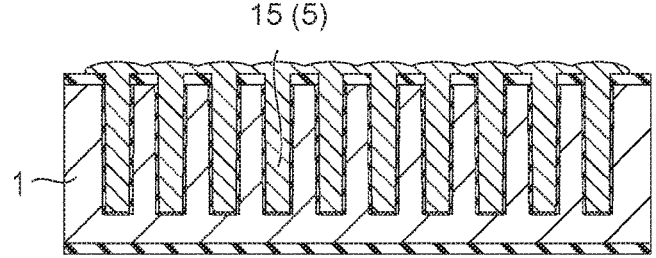

After being washed with water, the first insulating layer 20 around the edge of the silicon substrate 1 is partially removed with an aqueous solution of buffered hydrofluoric acid to expose the surface of the silicon substrate. A cathode is connected to the exposed portion of the silicon substrate 1, and gold plating is performed with a platinum-coated titanium mesh connected to an anode. The plating solution and the temperature thereof, and the current density are the same as in Example 1. A gold plating layer 15 is thus grown from the silicide layers 4 acting as a seed. The gold plating layer 15 is grown until protruding from the recessed portions, as shown in FIG. 9I, and the protruding gold portions are removed by CMP of the gold.

The resulting silicon substrate is subjected to ultrasonic cleaning in acetone for removing CMP slurry. The gold plating layer 15 in the recessed portions is not removed by nitrogen blowing for drying after ultrasonic cleaning. The metal portions 13 of the metal structure 5 each have a smallest width of 1.84 µm, a verticality of 89.9 degrees in the depth direction of the recessed portions, and an aspect ratio of about 54.

In examination through an X-ray microscope, clear high contrast image of the grating was obtained, and defects were not observed in the metal structure. It is thus confirmed that a structure has been obtained which includes a gold metal structure including gold metal portions disposed in recessed portions in a silicon substrate.

Example 5

Example 5 illustrates a method according to the fourth embodiment for manufacturing the structure of the first embodiment. The present Example is different from Example 4 in using an n-type semiconductor silicon substrate, forming reverse-tapered recessed portions, using a mixed gas of $CF_4$ and hydrogen as the first etching gas, using $NF_3$ and $ClF_3$ as the second etching gas, and others. The starting silicon substrate 1 used in the present Example is an n-type semiconductor silicon substrate having a diameter of 200 mm, a thickness of 500 µm and a resistivity of 0.02 Ωcm. The starting silicon substrate 1 is thermally oxidized at 1050° C. for 75 minutes to form an about 0.5 µm thick thermally oxidized film (first insulating layer) on the second surface and the third surface of the silicon substrate.

A positive resist is applied onto the thermally oxidized film on the second surface, and is then subjected to semiconductor photolithography so as to form a resist pattern having openings of 0.5 µm in width arranged at a pitch of 2 µm in four 130 mm×130 mm regions. Thus resist openings, each a linear opening having a width of 0.5 µm, are one-dimensionally arranged at a pitch of 2 µm in a striped manner. Then, the thermally oxidized film is subjected to reactive etching with $CF_4$ to partially expose the surface of the silicon substrate. Subsequently, the exposed silicon is subjected to anisotropic deep etching by ICP-RIE to form a plurality of recessed portions. This etching is performed up to a depth of about 10 µm and then stopped. Thus a plurality of 10 µm deep recessed portions are formed in the silicon substrate. The width of each recessed portion is 0.7 µm in the same plane as the top surfaces 8 and 0.67 µm at the bottom of the recessed portion. The verticality in the depth direction of the recessed portion is 89.8 degrees. Each recessed portion has an aspect ratio of 10/0.67 (=about 15). Subsequently, the resist is removed by UV ozone ashing, and then the silicon substrate is washed with hydrofluoroether and then a mixture of sulfuric acid and hydrogen peroxide. After being washed with water, the silicon substrate 1 is soaked with isopropyl alcohol and dried.

Then, the side walls and bottoms of the recessed portions formed by the etching are thermally oxidized at 1050° C. for 7 minutes to form an about 0.075 µm thick thermally oxidized film (second insulating layer).

Then, the thermally oxidized film is removed from the bottoms of the recessed portions to expose silicon at the bottoms. This partial removal of the thermally oxidized film is performed by dry etching using a mixed gas of $CF_4$ and hydrogen (flow rate ratio of 30:1) as the first etching gas.

Etching is continued for another 10 seconds from the moment when a portion of the silicon has been exposed in a region of the recessed portions 2 where the thermally oxidized film has been etched fastest. Consequently, the silicon substrate is etched to a depth of 0 to 0.01 µm from the surface thereof, and fluorocarbon polymer is deposited on the surfaces of the bottoms of the recessed portions. Subsequently, the fluorocarbon polymer deposited on the surface of the silicon substrate is removed by dry etching using a mixed gas of ammonium trifluoride ($NF_3$) and chlorine trifluoride ($ClF_3$) ((flow rate ratio of 50:1) as a second etching gas to expose the silicon surface at the bottoms of the recessed portions. In this operation, the verticality of the recessed portions in the depth direction is kept 89.8 degrees.

Subsequently, gold is deposited to a thickness of 50 nm in a vacuum sputtering apparatus, and a silicide layer 4 is formed at the bottoms of the recessed portions using a hot plate, in the same manner as in Example 4. The resulting silicon substrate is immersed in a solution containing iodine and potassium iodide for etching for removing the metal layer from the side walls 7 and the bottoms 8, as in Example 4. Then, after being washed with water, the silicon surface around the edge of the silicon substrate 1 is exposed for plating. Thus, a gold layer is deposited on the silicide layers by gold plating. The gold plating layer 15 is grown until protruding from the recessed portions, and the protruding gold portions are removed by CMP of the gold.

The resulting silicon substrate is subjected to ultrasonic cleaning in acetone for removing CMP slurry. The gold plating layer 15 in the recessed portions is not removed by nitrogen blowing for drying after ultrasonic cleaning. The metal portions of the metal structure each have a smallest width of 0.66 µm, a verticality of 90.2 degrees in the depth direction of the recessed portions, and an aspect ratio of about 15.

In examination through an X-ray microscope, clear high contrast image of the grating was produced, and defects were not observed in the metal structure. It is thus confirmed that a structure has been obtained which includes a metal structure including metal portions disposed in recessed portions in a silicon substrate.

Example 6

Example 6 illustrates a method according to the fourth embodiment for manufacturing the structure of the first embodiment. The present Example is different from Example 5 in the width and pitch of the recessed portions and in that etching operations for exposing the bottoms of the recessed portions are performed with a third and a fourth gas between the etching operations using the first and second gases. The operations from the forming of the recessed portions in the silicon substrate to the forming of the second insulating layer (FIG. 9C) are performed in the same manner as in Example 5, and thus description thereof was omitted. In these operations, however, patterning for forming a resist pattern having openings is performed, in view of forming recessed portions of 0.56 µm in width, in a different manner from Example 5 by semiconductor photolithography so that openings of 0.625 µm in width are one-dimensionally arranged at a pitch of 1.25 µm.

The thermally oxidized film is removed from the bottoms 3 of the recessed portions. In the present Example, a mixed gas of CF4 and hydrogen (flow rate ratio of 30:1) is used as the first gas, as in Example 5.

Etching is continued for another 30 seconds from the moment when a portion of the silicon has been exposed in a region of the recessed portions 2 where the thermally oxidized film has been etched fastest. Consequently, the silicon substrate is etched to a depth of 0 to 0.3 µm from the surface thereof, and fluorocarbon polymer is deposited on the surfaces of the bottoms of the recessed portions.

Subsequently, the deposited fluorocarbon polymer is removed using a third gas. The third gas is such that it can selectively etch the thermally oxidized film and silicon and exhibit higher etching performance on fluorocarbon polymer than the second gas. In the present Example, oxygen plasma ashing is performed for 120 seconds, using oxygen gas as the third gas. By removing the fluorocarbon polymer by oxygen plasma ashing, a silicon oxide film is formed on the silicon surface.

The silicon oxide film formed by the oxygen plasma ashing is removed using a fourth gas. Any etching gas can be used as the fourth gas as long as it is anisotropic and able to etch silicon oxide. The fourth gas may be the same as the first gas. In the present Example, the same mixed gas of CF4 and hydrogen as the first gas is used to remove the silicon oxide. Etching is continued for another 3 seconds from the moment when a portion of the silicon has been exposed in a region of the recessed portions where the thermally oxidized film has been etched fastest, thereby depositing fluorocarbon polymer on the silicon surfaces at the bottoms of the recessed portions. The thus deposited fluorocarbon polymer is thinner than the fluorocarbon polymer film at the moment of the completion of the etching with the first gas. This is because the time is shorter for etching continued from the moment when a portion of the silicon has been exposed in a region of the recessed portions where the thermally oxidized film has been etched fastest.

This fluorocarbon polymer is removed using the second gas. In the present Example, $NF_3$ and $ClF_3$ are used as the second gas, as in Example 5.

Thus, the silicon surface is exposed at the bottoms of the recessed portions by etching operations using the first, second, third and fourth etching gases. After the silicon surface is exposed, the operations are performed for forming the silicide layer at the bottoms of the recessed portions, removing the metal layer from the top surface and the side walls, filling the recessed portions by gold plating, and removing protruding gold portions, in the same manner as in Example 5. The resulting structure is the same as that of Example 5 except for the pitch of the recessed portions.

The present inventors have found that it is difficult to remove the fluorocarbon polymer deposited on the bottoms of the recessed portions with a desired width of the recessed portions maintained. When the recessed portions have a smaller width and a large depth, the etching rate of the bottoms thereof is reduced. It has been however found that the silicon surface can be exposed at the bottoms of the recessed portions with a desired width of the recessed portions maintained, by etching using the third and fourth etching gases as in the present Example, even if a large amount of fluorocarbon polymer is deposited. If the width of the recessed portions is 1 µm or less, the fluorocarbon polymer may not be removed with a desired width of the recessed portions maintained only by the etching using the second gas, which may further etch the insulating layer on the side walls of the recessed portions.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-151202, filed Jul. 24, 2014, and Japanese Patent Application No. 2015-110210, filed May 29, 2015, which are hereby incorporated by reference herein in their entirety.

What is claimed is:

1. An X-ray Talbot interferometer comprising:
   an X-ray diffraction grating capable of diffracting x-ray radiation from an X-ray source to form an interference pattern;
   an X-ray shield grating capable of partially blocking the X-ray radiation forming the interference pattern; and
   an X-ray detector capable of detecting X-ray radiation from the X-ray shield grating;
   wherein the X-ray shield grating includes:
   a silicon substrate having a plurality of recessed portions, each recessed portion having a bottom and a side wall;
   silicide layers, each silicide layer disposed in one of the plurality of recessed portions and in contact with the bottom of the one of the plurality of recessed portions; and
   a metal structure including metal portions, each metal portion disposed in one of the plurality of recessed portions.

2. An X-ray Talbot interferometer comprising:
   an X-ray shield grating capable of dividing X-ray radiation from an X-ray source;
   an X-ray diffraction grating capable of diffracting the X-ray radiation from the X-ray shield grating to form an interference pattern; and
   an X-ray detector capable of detecting at least part of the X-ray radiation forming the interference pattern;
   wherein the X-ray shield grating includes:
   a silicon substrate having a plurality of recessed portions, each recessed portion having a bottom and a side wall;
   silicide layers, each silicide layer disposed in one of the plurality of recessed portions and in contact with the bottom of the one of the plurality of recessed portions; and
   a metal structure including metal portions, each metal portion disposed in one of the plurality of recessed portions.

* * * * *